US009840118B2

(12) United States Patent
Singh

(10) Patent No.: US 9,840,118 B2
(45) Date of Patent: Dec. 12, 2017

(54) TIRE SENSOR-BASED ROBUST ROAD SURFACE ROUGHNESS CLASSIFICATION SYSTEM AND METHOD

(71) Applicant: The Goodyear Tire & Rubber Company, Akron, OH (US)

(72) Inventor: Kanwar Bharat Singh, Stow, OH (US)

(73) Assignee: The Goodyear Tire & Rubber Company, Akron, OH (US)

( * ) Notice: Subject to any disclaimer, the term of this patent is extended or adjusted under 35 U.S.C. 154(b) by 99 days.

(21) Appl. No.: 14/964,029

(22) Filed: Dec. 9, 2015

(65) Prior Publication Data

US 2017/0166019 A1    Jun. 15, 2017

(51) Int. Cl.
| | |
|---|---|
| *G01M 17/02* | (2006.01) |
| *B60C 23/04* | (2006.01) |
| *G01N 19/00* | (2006.01) |
| *B60W 40/06* | (2012.01) |
| *B60C 13/00* | (2006.01) |

(52) U.S. Cl.
CPC ...... *B60C 23/0474* (2013.01); *B60C 23/0408* (2013.01); *B60C 23/0415* (2013.01); *B60W 40/06* (2013.01); *G01N 19/00* (2013.01); *B60C 13/00* (2013.01); *B60G 2400/821* (2013.01); *B60G 2800/162* (2013.01); *B60T 2210/12* (2013.01); *B60T 2210/14* (2013.01)

(58) Field of Classification Search
None
See application file for complete search history.

(56) References Cited

U.S. PATENT DOCUMENTS

| | | | |
|---|---|---|---|
| 4,958,306 A * | 9/1990 | Powell | G01C 7/04 |
| | | | 702/40 |
| 5,260,683 A | 11/1993 | Tanaka et al. | |
| 5,553,491 A | 9/1996 | Naito et al. | |
| 5,826,207 A | 10/1998 | Ohashi et al. | |
| 6,539,295 B1 | 3/2003 | Katzen et al. | |
| 6,662,097 B2 * | 12/2003 | Kin | B60T 8/172 |
| | | | 701/70 |
| 6,962,075 B2 | 11/2005 | Bertrand | |
| 7,240,542 B2 | 7/2007 | Gustafsson et al. | |
| 7,404,317 B2 | 7/2008 | Mancosu et al. | |
| 7,404,319 B2 | 7/2008 | Poulbot et al. | |

(Continued)

FOREIGN PATENT DOCUMENTS

| | | | |
|---|---|---|---|
| EP | 1378378 A1 | 1/2004 | |
| EP | 1661737 A2 | 5/2006 | |

(Continued)

OTHER PUBLICATIONS

Pages 1 through 29, "Slip-based Tire-road Friction Estimation" by Fredrik Gustafsson, Department of Electrical Engineering, Linköping University, Linköping, Sweden. Nov. 28, 1996.

(Continued)

*Primary Examiner* — Andre Allen
(74) *Attorney, Agent, or Firm* — Edward T. Kennedy

(57) ABSTRACT

A road classification system for determining a road surface condition includes a model having as an input changes in the measured axle vertical acceleration of the vehicle. The model further uses a sensor-measured tire inflation pressure and a tire construction type ascertained from a tire-based identification tag.

14 Claims, 32 Drawing Sheets

(56) References Cited

U.S. PATENT DOCUMENTS

| | | |
|---|---|---|
| 7,415,874 B2 | 8/2008 | Mancosu et al. |
| 7,546,764 B2 | 6/2009 | Morinaga |
| 7,549,327 B2 | 6/2009 | Breed |
| 7,552,628 B2 | 6/2009 | Mancosu |
| 7,681,960 B2 | 3/2010 | Wanke et al. |
| 7,856,871 B2 | 12/2010 | Mancosu et al. |
| 7,908,918 B2 | 3/2011 | Brusarosco et al. |
| 7,945,361 B2 | 5/2011 | Brusarosco et al. |
| 7,954,367 B2 | 6/2011 | Mancosu et al. |
| 8,051,705 B2 | 11/2011 | Kobayakawa |
| 8,155,798 B2 | 4/2012 | Seiniger et al. |
| 8,316,700 B2 | 11/2012 | Brusarosco et al. |
| 8,371,159 B2 | 2/2013 | Morinaga |
| 8,483,976 B2 | 7/2013 | Morinaga |
| 8,844,346 B1 | 9/2014 | Singh et al. |
| 2002/0162389 A1 | 11/2002 | Yokota et al. |
| 2003/0058118 A1 | 3/2003 | Wilson |
| 2003/0121319 A1 | 7/2003 | Kojima et al. |
| 2007/0255510 A1 | 11/2007 | Mancosu et al. |
| 2008/0103659 A1 | 5/2008 | Mancosu |
| 2009/0055040 A1 | 2/2009 | Nagaya |
| 2010/0019964 A1* | 1/2010 | Huang .............. G01M 17/06 342/357.31 |
| 2010/0030533 A1* | 2/2010 | Ueda ................ G01M 17/02 703/2 |
| 2011/0199201 A1 | 8/2011 | Brusarosco et al. |
| 2015/0284006 A1 | 10/2015 | Singh |
| 2016/0201277 A1* | 7/2016 | Svantesson ........... E01C 23/01 73/146 |

FOREIGN PATENT DOCUMENTS

| | | | | |
|---|---|---|---|---|
| EP | 1757464 A1 | 2/2007 | | |
| EP | 1964736 A1 | 9/2008 | | |
| EP | 2301769 A1 | 3/2011 | | |
| EP | 2138372 A1 | 8/2012 | | |
| EP | 2774784 A1 | 9/2014 | | |
| EP | 2927065 A1 * | 10/2015 | ............ | B60C 23/02 |
| JP | 2005-249525 | 9/2005 | | |
| WO | 02092364 A2 | 11/2002 | | |
| WO | 03022651 A1 | 3/2003 | | |
| WO | WO 2008069729 A1 * | 6/2008 | | |
| WO | WO2011054363 A1 | 5/2011 | | |
| WO | WO 2017064734 A1 * | 4/2017 | .......... | G01M 17/007 |

OTHER PUBLICATIONS

Pages 607 through 617, "Estimation of the Maximum Tire-road Friction Coefficient" by Steffen Müller, et al., Journal of Dynamic Systems, Measurement, and Control. Dec. 2003, vol. 125.

Page 454 through 458, "Real-time Slip-based Estimation of Maximum Tire-road Friction Coefficient" by Lee et al., IEFF/ASME Transactions on Mechatronics. Jun. 2004, vol. 9, No. 2.

"Experimental Analysis of Potentials for Tire Friction Estimation in Low-slip Operating Mode" by Pavkovi et al., reprinted from Vehicle Dynamics and Simulation 2006, SAE International, 400 Commonwealth Drive, Warrendale, PA 15096-0001 . Apr. 306, 2006.

Pages 1, 2, 5 and 120 through 169, "Tire Modeling and Friction Estimation" by Jacob Svendenius Department of Automatic Control, Lund University, Lund, Sweden. Apr. 2007.

Pages 3948 through 2953, "Robust Estimation of Road Friction Coefficient" by Ahn, et al. 2011 American Control Conference. Jun. 29 through Jul. 1, 2011.

Pages 1183 through 1195, Algorithms for Real-time Estimation of Individual Wheel Tire-road Friction Coefficients by Rajamani, et al., IEFF/ASME Transactions on Mechatronics. Dec. 2012, vol. 17, No. 6.

EPO Search Report received by Applicant dated Apr. 3, 2017.

* cited by examiner

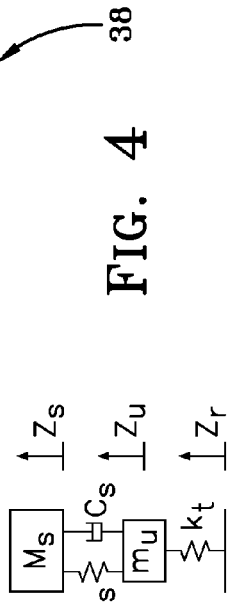

FIG. 4

Effects of Vehicle and Tire Characteristics on Axle Acceleration: Sensitivity Study

| Case | Description | Dependency of the root-mean-square (RMS) value of the axle vertical acceleration on vehicle configuration parameters | | | | |
|---|---|---|---|---|---|---|
| | | Vehicle Loading State | Tire | | Suspension | |
| | | Sprung Mass [%] | Tire Stiffness [%] | Tire Stiffness [%] | Stiffness [%] | Damping [%] |
| 1 | Normal Conditions | 100 | 100 | | 100 | 100 |
| 2 | Increasing load | 150 | 100 | | 100 | 100 |
| 3 | Decreasing tire stiffness | 100 | 50 | | 100 | 100 |
| 4 | Increasing tire stiffness | 100 | 150 | | 100 | 100 |
| 5 | Decreasing suspension stiffness | 100 | 100 | | 50 | 100 |
| 7 | Increasing suspension stiffness | 100 | 100 | | 100 | 100 |
| 8 | Decreasing suspension damping | 100 | 100 | | 100 | 50 |
| 9 | Increasing suspension damping | 100 | 100 | | 100 | 150 |

Nominal Parameters of QC Model
Ms=450; % Quarter sprung mass (kg)
mu=45; % Unsprung mass (kg)
Ks=27*1000; % Passive spring stiffness (N/m)
Cs=900; % Passive damping constant (Ns/m)
Kt=232*1000; % Tire stiffness (N/m)

Change in RMS Value of the Axle Vertical Acceleration for Different Vehicle Configurations ⟵ 40

| Case | Description | RMS Value of the Axle Acceleration [m/s^2] | % Change |
|---|---|---|---|
| 1 | Normal Conditions | 15.02 | — |
| 2 | Increasing load | 15.13 | 0.0% |
| 3 | Decreasing tire stiffness | 6.29 | -58% |
| 4 | Increasing tire stiffness | 22.91 | +46% |
| 5 | Decreasing suspension stiffness | 15.00 | 0.0% |
| 7 | Increasing suspension stiffness | 15.06 | 0.0% |
| 8 | Decreasing suspension damping | 22.26 | +46% |
| 9 | Increasing suspension damping | 12.02 | -20% |

The main variations in RMS value of the axle acce;eration are occurring for a change in:

1) Tire stiffness (usually happening as a result of the change in the tire inflation pressure).
2) Suspension damping respectively.

FIG. 5

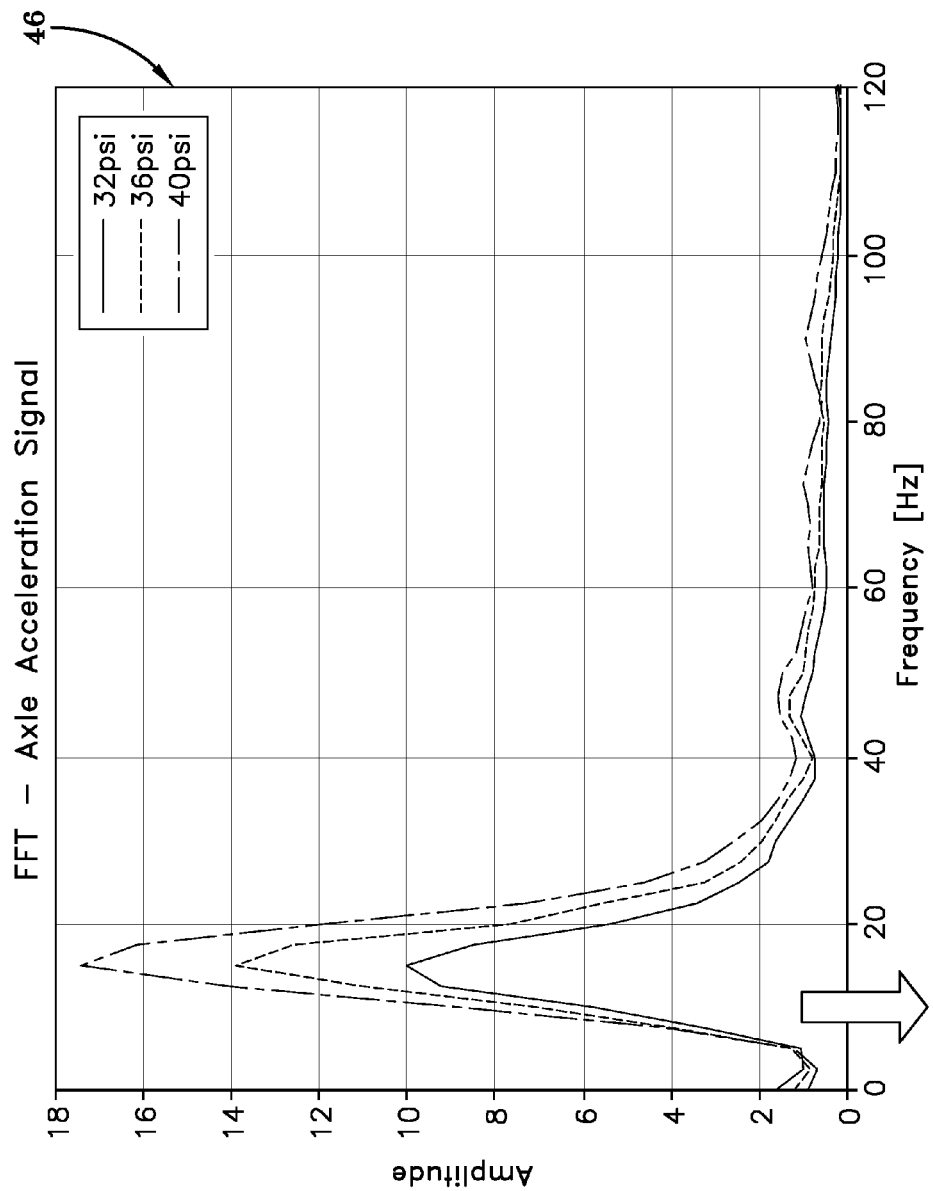

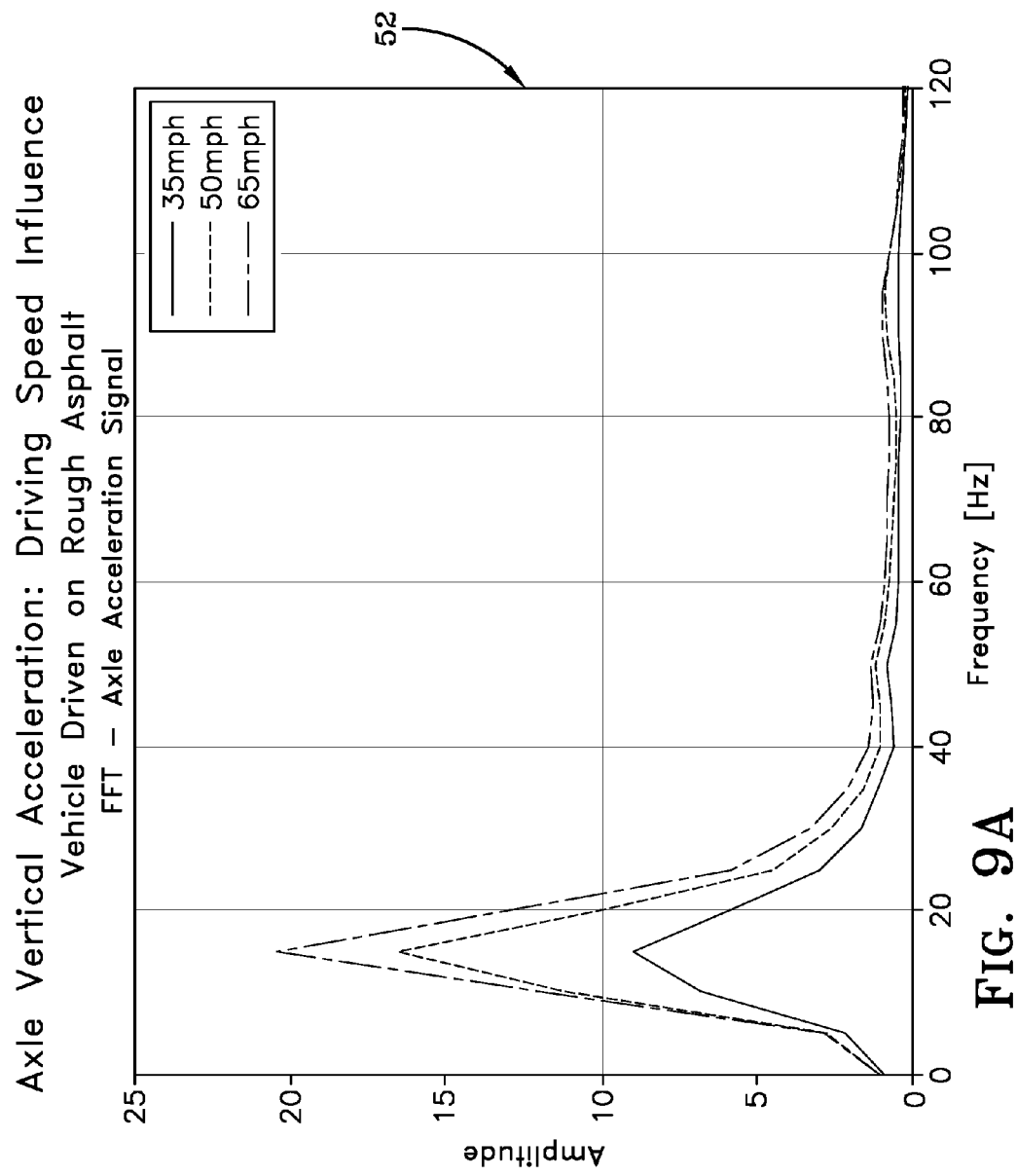

TIRE SENSOR-BASED ROBUST ROAD SURFACE ROUGHNESS CLASSIFICATION SYSTEM AND METHOD

FIELD OF THE INVENTION

The invention relates generally a system and method for classifying road surface roughness and, more particularly, to such systems employing vehicle-based sensor data.

BACKGROUND OF THE INVENTION

Road surface roughness has an effect on many vehicle operating systems including steering, braking and suspension performance. The detection of road surface conditions in real time for use as an input to such systems, however, has proven problematic. There, accordingly, remains a need for a robust system and method for accurately monitoring and classifying road roughness in real time for use by vehicle systems in adjusting vehicle control parameters that are sensitive to road roughness variation.

SUMMARY OF THE INVENTION

According to an aspect of the invention, a road classification system includes a tire-mounted sensor operable to measure a tire inflation pressure; a tire-mounted identification tag operable to identify the one tire by an identification code; a tire construction database operable for identifying a tire construction type for the one tire from the identification code; a vehicle-mounted axle vertical acceleration sensor operable to measure an axle vertical acceleration of the vehicle; and a road surface classification model for making a road surface condition conclusion based on changes in the measured axle vertical acceleration of the vehicle, the measured tire inflation pressure and the identified tire construction type.

In another aspect, the system further includes a vehicle-mounted speed sensor operable to measure a vehicle speed and a vehicle-mounted sensor operable to indicate a suspension damper setting, the road surface classification model making the road surface condition conclusion based on the measured vehicle speed and the suspension damper setting.

In a still further aspect of the invention, the measured tire inflation pressure and the identified tire construction are employed in determining a tire sidewall stiffness and the road surface classification model makes the road surface condition conclusion based on changes in the measured axle vertical acceleration of the vehicle, a measured damping of a main suspension of the vehicle and the vertical stiffness of the one tire.

DEFINITIONS

"ANN" or "Artificial Neural Network" is an adaptive tool for non-linear statistical data modeling that changes its structure based on external or internal information that flows through a network during a learning phase. ANN neural networks are non-linear statistical data modeling tools used to model complex relationships between inputs and outputs or to find patterns in data.

"Aspect ratio" of the tire means the ratio of its section height (SH) to its section width (SW) multiplied by 100 percent for expression as a percentage.

"Asymmetric tread" means a tread that has a tread pattern not symmetrical about the center plane or equatorial plane EP of the tire.

"Axial" and "axially" means lines or directions that are parallel to the axis of rotation of the tire.

"CAN bus" is an abbreviation for controller area network.

"Chafer" is a narrow strip of material placed around the outside of a tire bead to protect the cord plies from wearing and cutting against the rim and distribute the flexing above the rim.

"Circumferential" means lines or directions extending along the perimeter of the surface of the annular tread perpendicular to the axial direction.

"Equatorial Centerplane (CP)" means the plane perpendicular to the tire's axis of rotation and passing through the center of the tread.

"Footprint" means the contact patch or area of contact created by the tire tread with a flat surface as the tire rotates or rolls.

"Groove" means an elongated void area in a tire wall that may extend circumferentially or laterally about the tire wall. The "groove width" is equal to its average width over its length. A grooves is sized to accommodate an air tube as described.

"Inboard side" means the side of the tire nearest the vehicle when the tire is mounted on a wheel and the wheel is mounted on the vehicle.

"Kalman Filter" is a set of mathematical equations that implement a predictor-corrector type estimator that is optimal in the sense that it minimizes the estimated error covariance, when some presumed conditions are met.

"Lateral" means an axial direction.

"Lateral edges" means a line tangent to the axially outermost tread contact patch or footprint as measured under normal load and tire inflation, the lines being parallel to the equatorial centerplane.

"Luenberger Observer" is a state observer or estimation model. A "state observer" is a system that provide an estimate of the internal state of a given real system, from measurements of the input and output of the real system. It is typically computer-implemented, and provides the basis of many practical applications.

"MSE" is an abbreviation for Mean square error, the error between and a measured signal and an estimated signal which the Kalman Filter minimizes.

"Net contact area" means the total area of ground contacting tread elements between the lateral edges around the entire circumference of the tread divided by the gross area of the entire tread between the lateral edges.

"Non-directional tread" means a tread that has no preferred direction of forward travel and is not required to be positioned on a vehicle in a specific wheel position or positions to ensure that the tread pattern is aligned with the preferred direction of travel. Conversely, a directional tread pattern has a preferred direction of travel requiring specific wheel positioning.

"Outboard side" means the side of the tire farthest away from the vehicle when the tire is mounted on a wheel and the wheel is mounted on the vehicle.

"Peristaltic" means operating by means of wave-like contractions that propel contained matter, such as air, along tubular pathways.

"Piezoelectric Film Sensor" a device in the form of a film body that uses the piezoelectric effect actuated by a bending of the film body to measure pressure, acceleration, strain or force by converting them to an electrical charge.

"PSD" is Power Spectral Density (a technical name synonymous with FFT (Fast Fourier Transform).

"Radial" and "radially" means directions radially toward or away from the axis of rotation of the tire.

"Rib" means a circumferentially extending strip of rubber on the tread which is defined by at least one circumferential groove and either a second such groove or a lateral edge, the strip being laterally undivided by full-depth grooves.

"Sipe" means small slots molded into the tread elements of the tire that subdivide the tread surface and improve traction, sipes are generally narrow in width and close in the tires footprint as opposed to grooves that remain open in the tire's footprint.

"Tread element" or "traction element" means a rib or a block element defined by having a shape adjacent grooves.

"Tread Arc Width" means the arc length of the tread as measured between the lateral edges of the tread.

BRIEF DESCRIPTION OF THE DRAWINGS

The invention will be described by way of example and with reference to the accompanying drawings in which:

FIG. 4 is a table showing effects of vehicle and tire characteristics on axle acceleration as the result of a sensitivity study.

FIG. 5 is a table showing change in RMS value of the axle vertical acceleration for different vehicle configurations.

FIG. 7B is an enlarged representation of the identified segment of the FIG. 7A graph showing FFT axle acceleration signal at the three tire inflation levels.

FIGS. 9A and 9B are graphs of axle vertical acceleration of a vehicle over rough asphalt, at the three tire inflation levels.

DETAILED DESCRIPTION OF THE INVENTION

Figure 1:
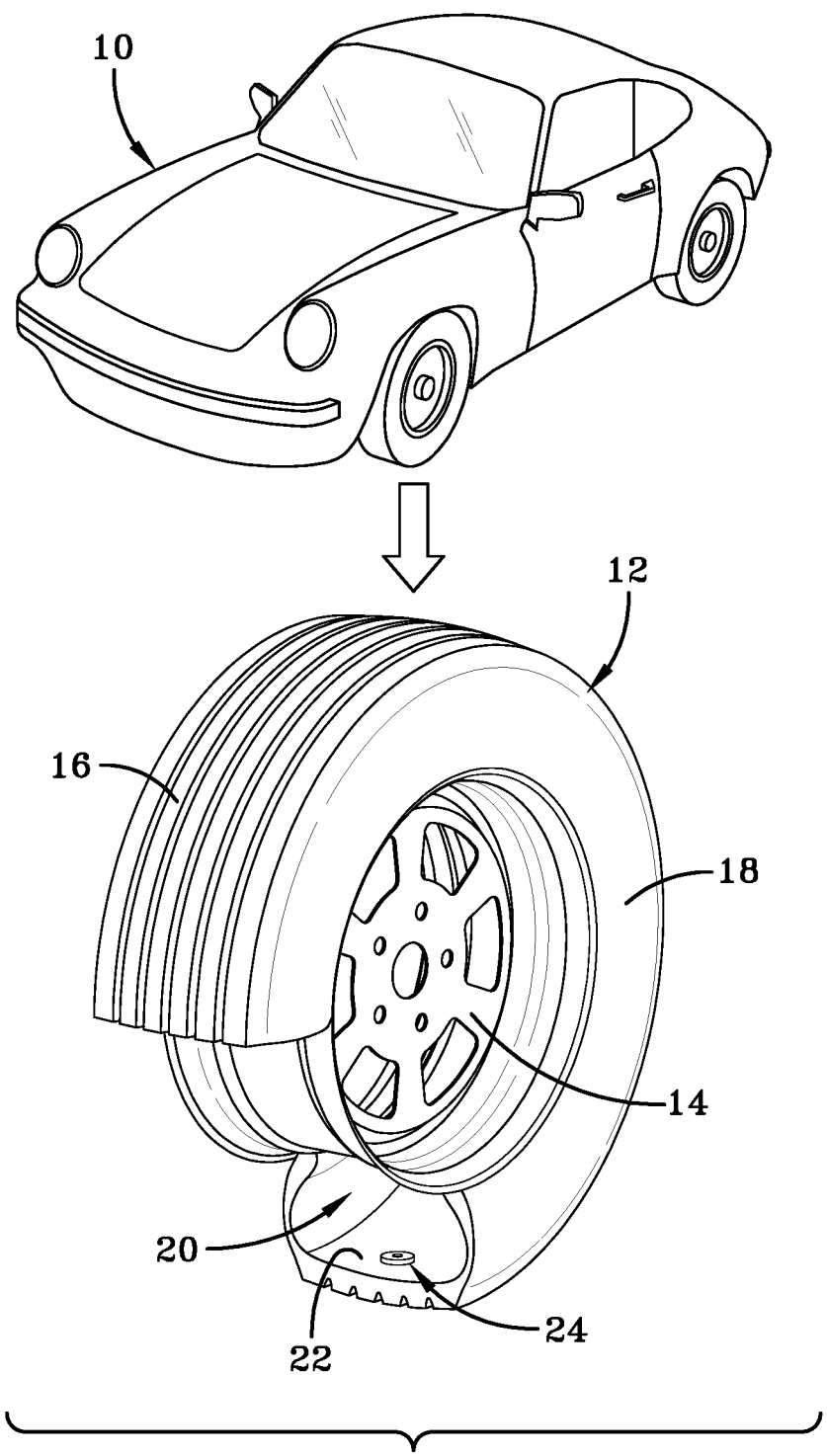
FIG. 1 is an enlarged schematic of a vehicle and representative wheel.

Referring to FIG. 1, the subject road classification system is useful to a vehicle 10 having tires 12 mounted to rims 14. The vehicle shown is a passenger car but the subject system and method applies equally to other vehicle types. The tire 12 is of conventional construction having a tread 16, sidewalls 18 and inner liner 22 defining an air cavity 20. A tire pressure monitoring system (TPMS) module 24 is secured to the tire inner liner 22 and includes an air pressure sensor, a transmitter for transmitting cavity air pressure measurements. In addition, the TPMS module 24 has a tire identification (tire ID) tag that identifies a unique tire code for the purpose of identifying tire construction type. From the tire identification code, the tire may be uniquely identified and its construction type ascertained from a database.

Figure 2A:
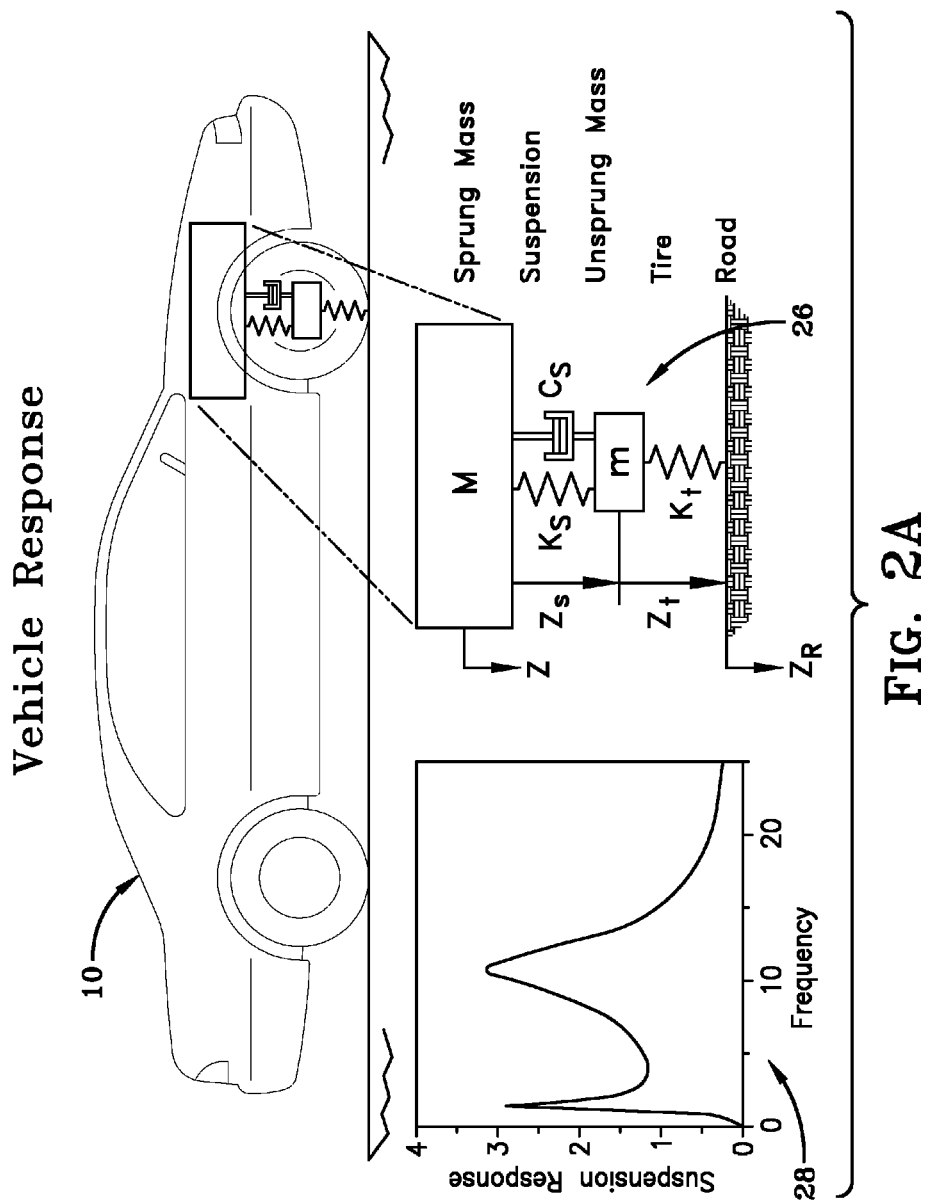
FIG. 2A is a vehicle and suspension model and associated graph of suspension response to frequency.

In reference to FIG. 2A, a suspension model 26 is shown with graph 28 of suspension response to frequency plotted. The major purpose of any vehicle suspension is to isolate the body from road unevenness disturbances and to maintain the contact between the road and the wheel. Therefore, it is the suspension system that is responsible for the ride quality and driving stability. With a priori information of the road roughness, a superior performance can be achieved, and this information can be obtained from vehicle-based road classification methods that use axle vertical acceleration signals.

Road classification methods typically use RMS values of axle accelerations. As will be seen from the following, the subject system and method identifies and uses the effects of vehicle and tire characteristics on axle vertical accelerations for use in road classification. The subject system and method identifies the main influences on RMS as damping of the main suspension and tire vertical stiffness.

The system and method uses available TPMS sensor module 24 to provide tire inflation pressure and tire ID information in order to enable implementation of a robust road classification system and method that is capable of accounting for the changes in RMS values of axle accelerations due to a variation in the tire inflation pressure or tire construction type/make.

Figure 2B:
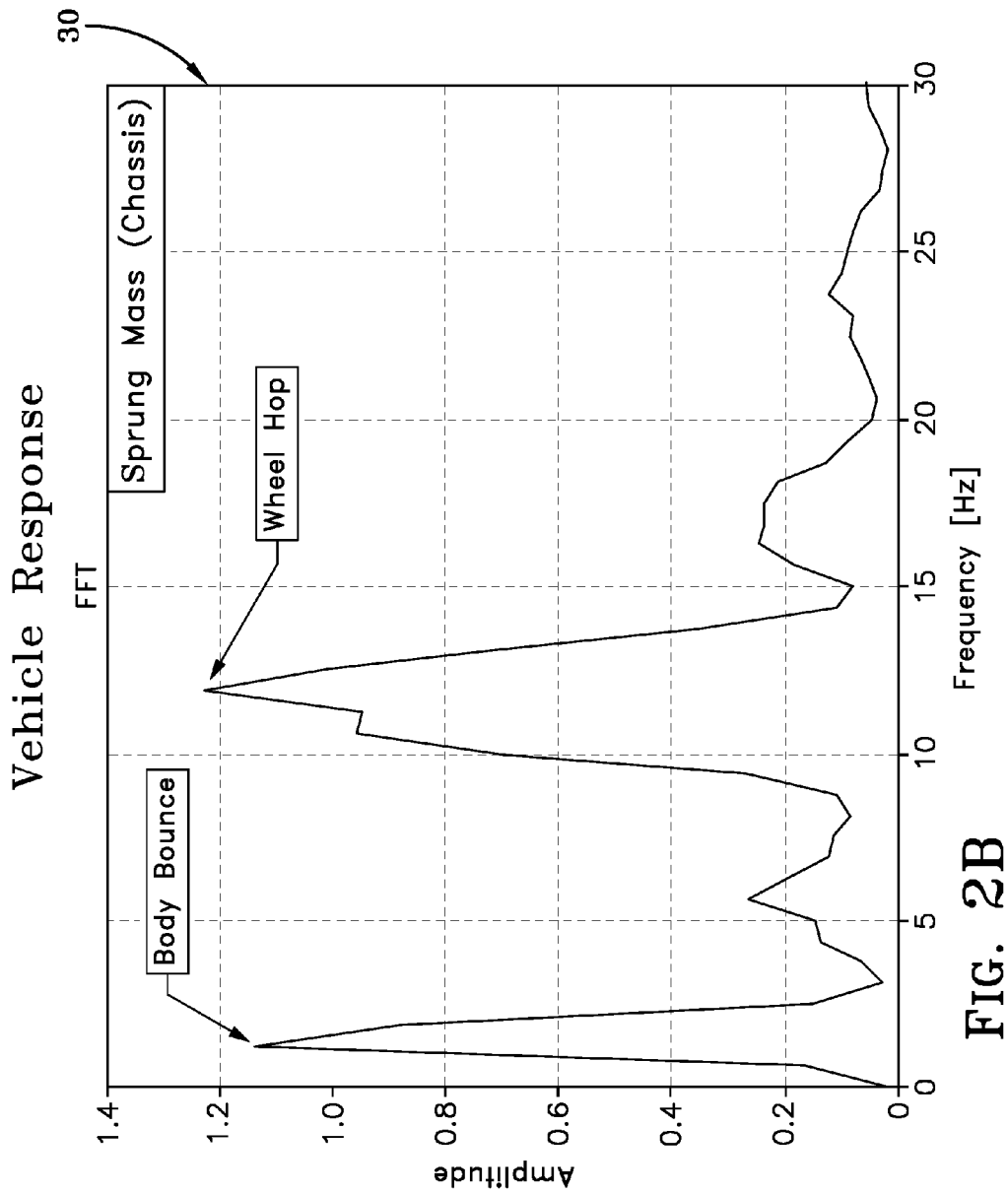
FIG. 2B is a vehicle response graph of sprung mass (chassis) amplitude to frequency showing body bounce and wheel hop points.
Figure 2C:
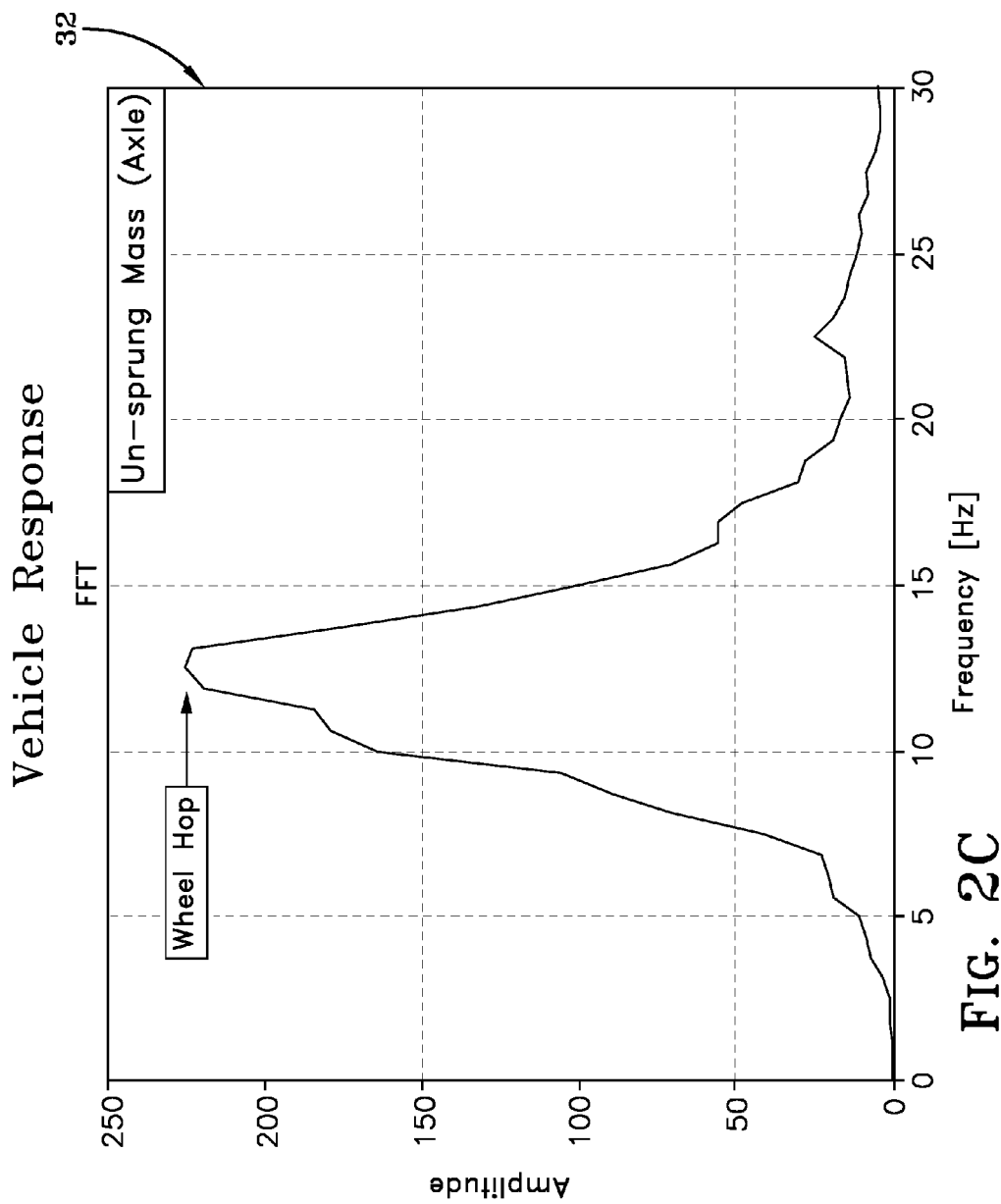
FIG. 2C is a vehicle response graph of un-sprung mass (axle) amplitude to frequency and showing wheel hop peak.
Figure 3A:
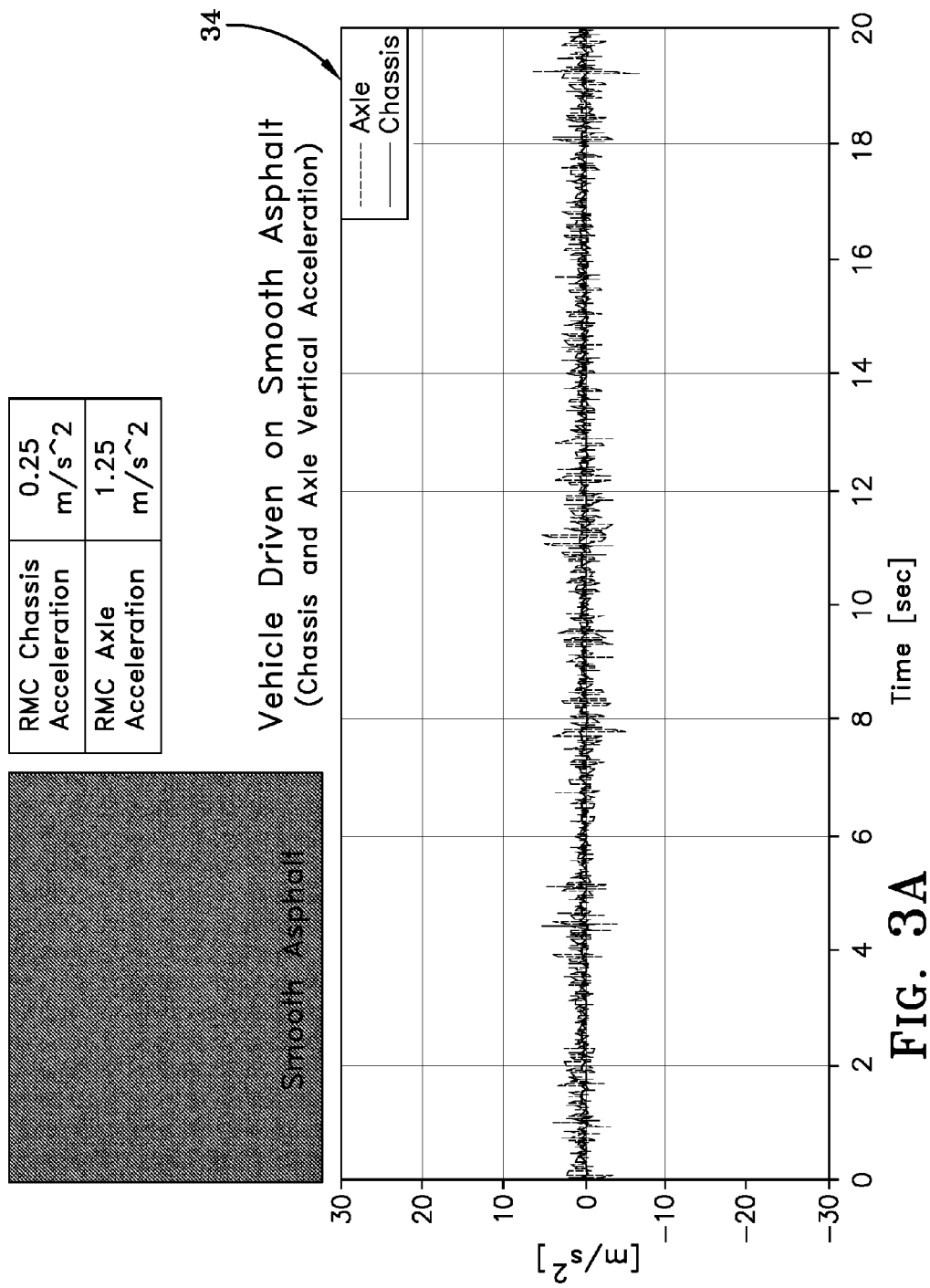
FIG. 3A is a vehicle response on smooth asphalt showing chassis and axle vertical acceleration on smooth asphalt.
Figure 3B:
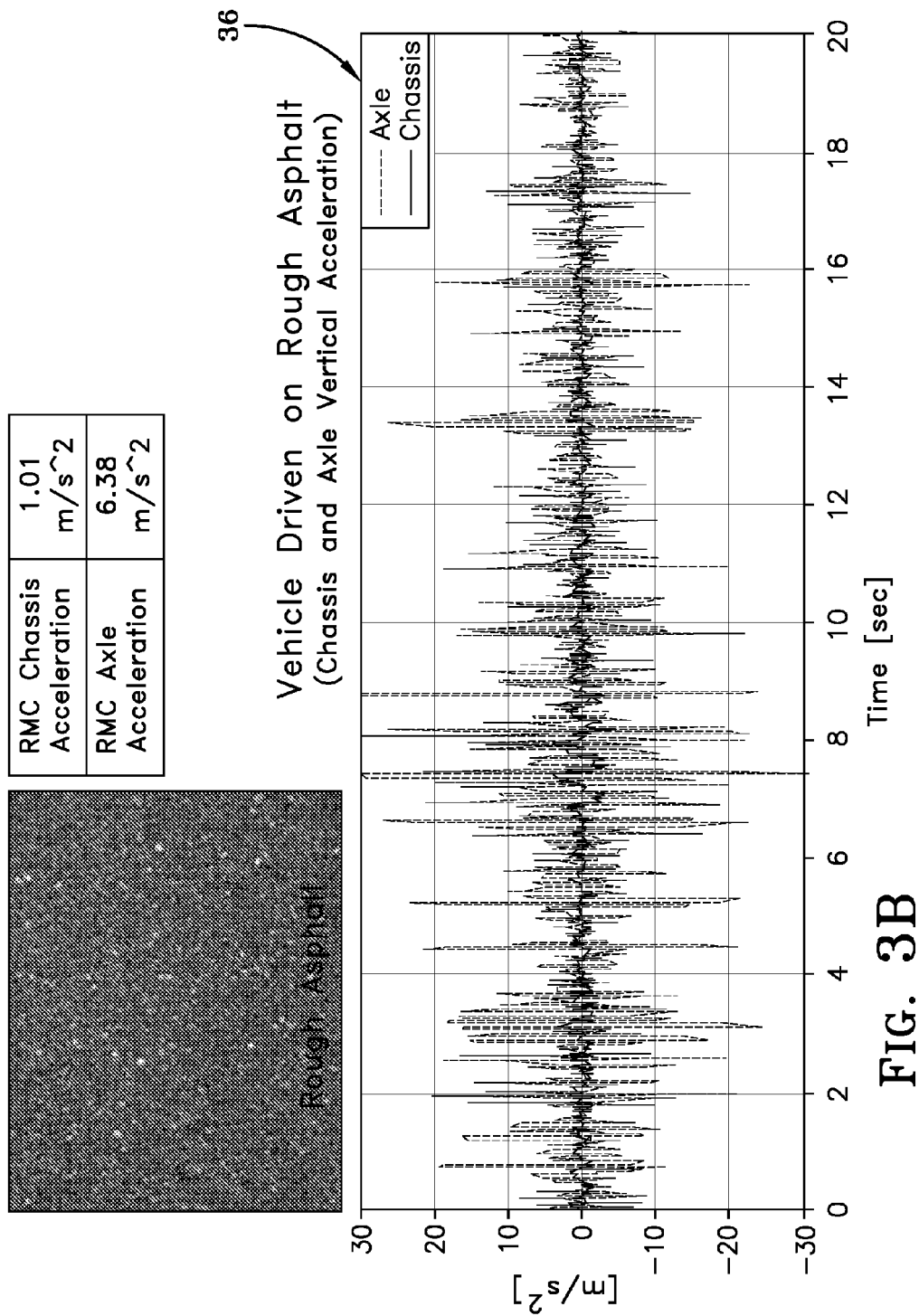
FIG. 3B is a vehicle response on smooth asphalt showing chassis and axle vertical acceleration on rough asphalt.

With reference to FIGS. 2B and 2C, from the sprung mass (chassis) graph 30 body bounce and wheel hop peaks may be identified. The frequency response of a typical passenger car extends from approximately 0.5 to 20 Hz. The unsprung mass (axle) frequency response graph 32 shows the identified wheel hop peak. In FIG. 3A the vehicle response graph 34 is shown (chassis and axle vertical acceleration) for a smooth asphalt surface while FIG. 3B shows in graph 36 the vehicle response on rough asphalt. From these graphs, it will be seen that the vertical acceleration of the axle is a good indicator of the road roughness level.

From the table 38 in FIG. 4, results of a sensitivity study are summarized. The effects of vehicle and tire characteristics on axle acceleration are represented in nine cases. Sprung mass, tire stiffness and suspension columns are represented in percentages for the nine case conditions under "Description". The table 38 indicates a dependency of the root-mean-square (RMS) value of the axle vertical acceleration on vehicle configuration parameters.

The effect of change in RMS value of the axle vertical acceleration for different vehicle configurations is summarized in table 40 of FIG. 5. RMS value of the axle acceleration and percent change columns for the nine listed conditions in the "Description" column show that the main variations in RMS value of the axle acceleration are occurring for a change in:

(1) tire stiffness (usually happening as the result of a change in the tire inflation pressure) and (2) suspension damping respectively.

Figure 6:
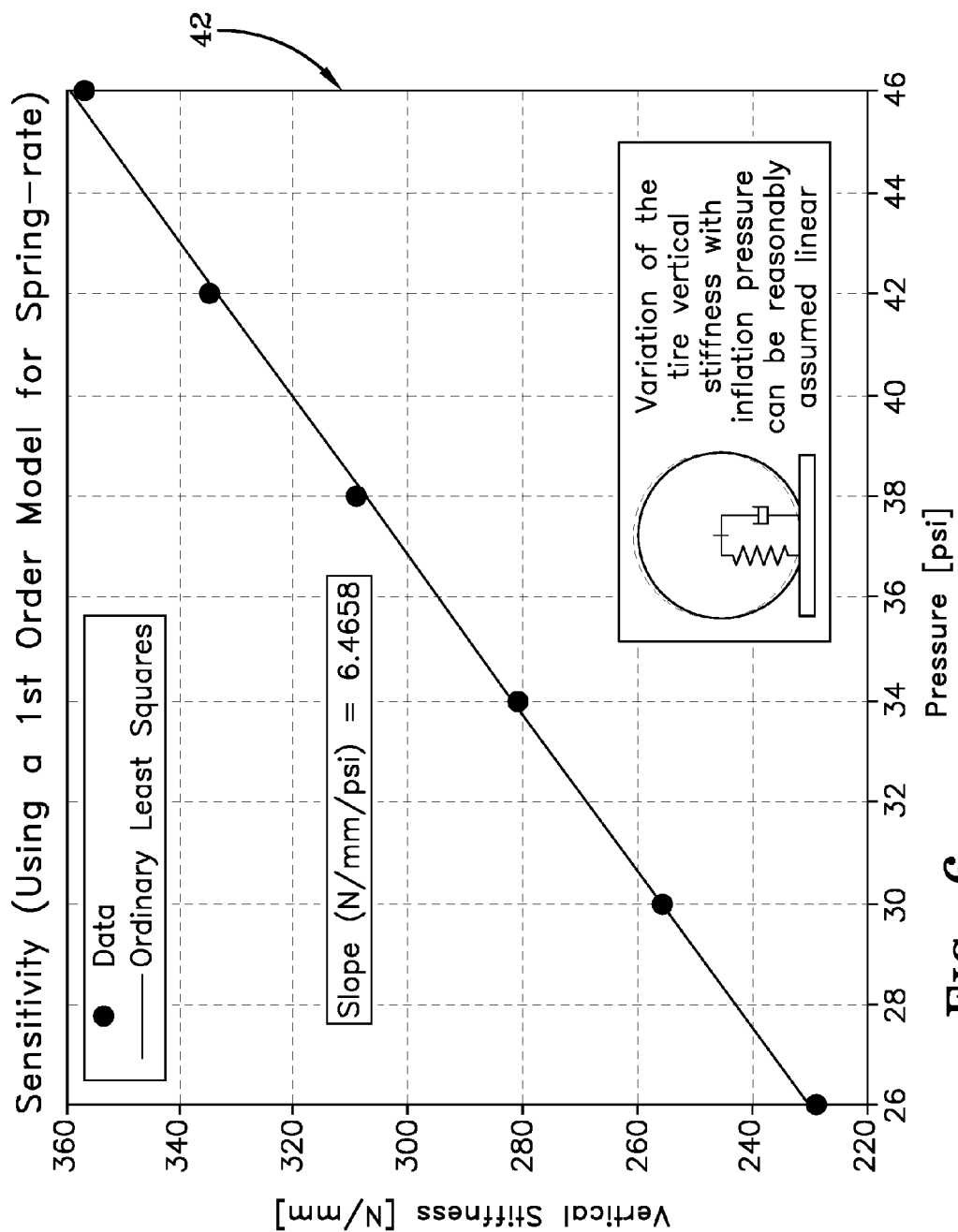
FIG. 6 is a graph of vertical stiffness to pressure showing sensitivity using a first order model for spring-rate.

The influence of inflation pressure on the tire vertical stiffness will be seen from the graph 42 of FIG. 6 that uses a first order model shown for spring-rate. For the test, a Goodyear Eagle FI Asymmetric tire size 255/45R19 was used. The graph seen of vertical stiffness to inflation pressure confirms that variation of tire vertical stiffness with inflation pressure can be reasonably assumed linear.

Figure 7A:
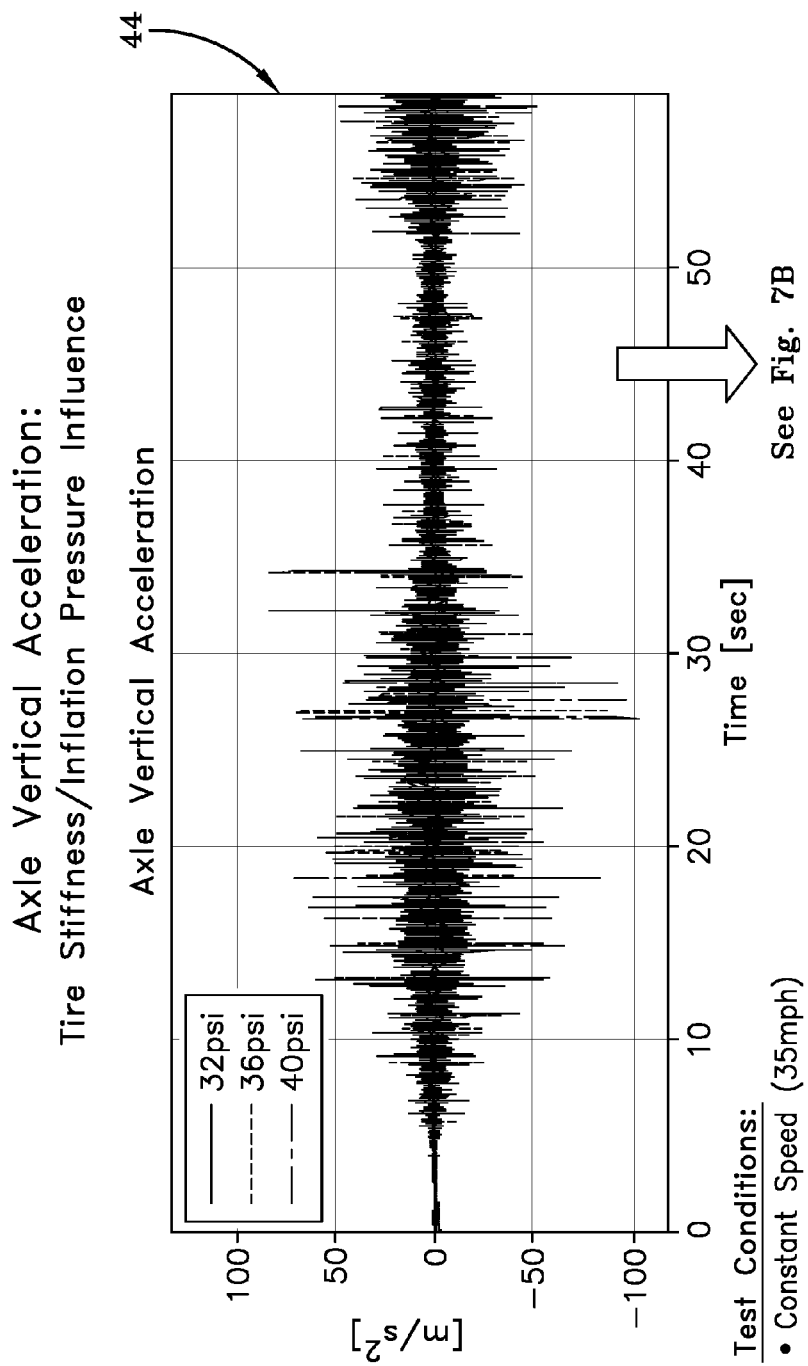
FIG. 7A is a graph of axle vertical acceleration at three distinct values of tire inflation pressure.
Figure 7C:
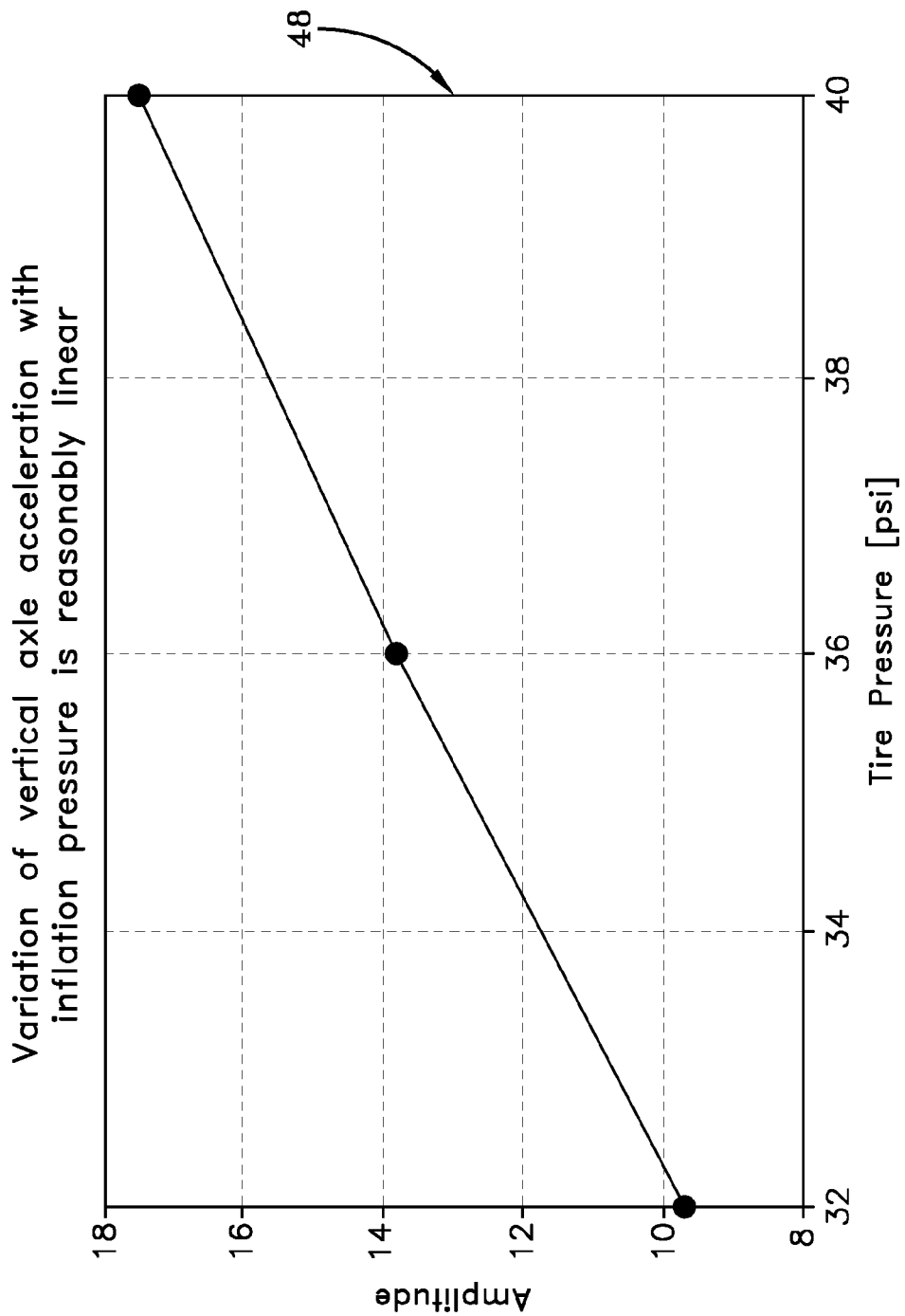
FIG. 7C is a graph showing the variation of vertical axle acceleration with inflation pressure.

In graph 44 of FIG. 7A, the influence of tire stiffness/inflation pressure on axle vertical acceleration will be seen. For the test conditions listed in FIG. 7A, the axle vertical acceleration is plotted in graph 44, while enlarged graph 46 of FIG. 7B constituting the designated segment of FIG. 7A is provided. Graph 46 represents the FFT-axle acceleration signal amplitude to frequency for three tire inflations (32, 36, and 40 psi). From the graph 48 of amplitude to tire pressure, it was confirmed that variation of vertical axle acceleration with inflation pressure is reasonably linear.

Figure 8:
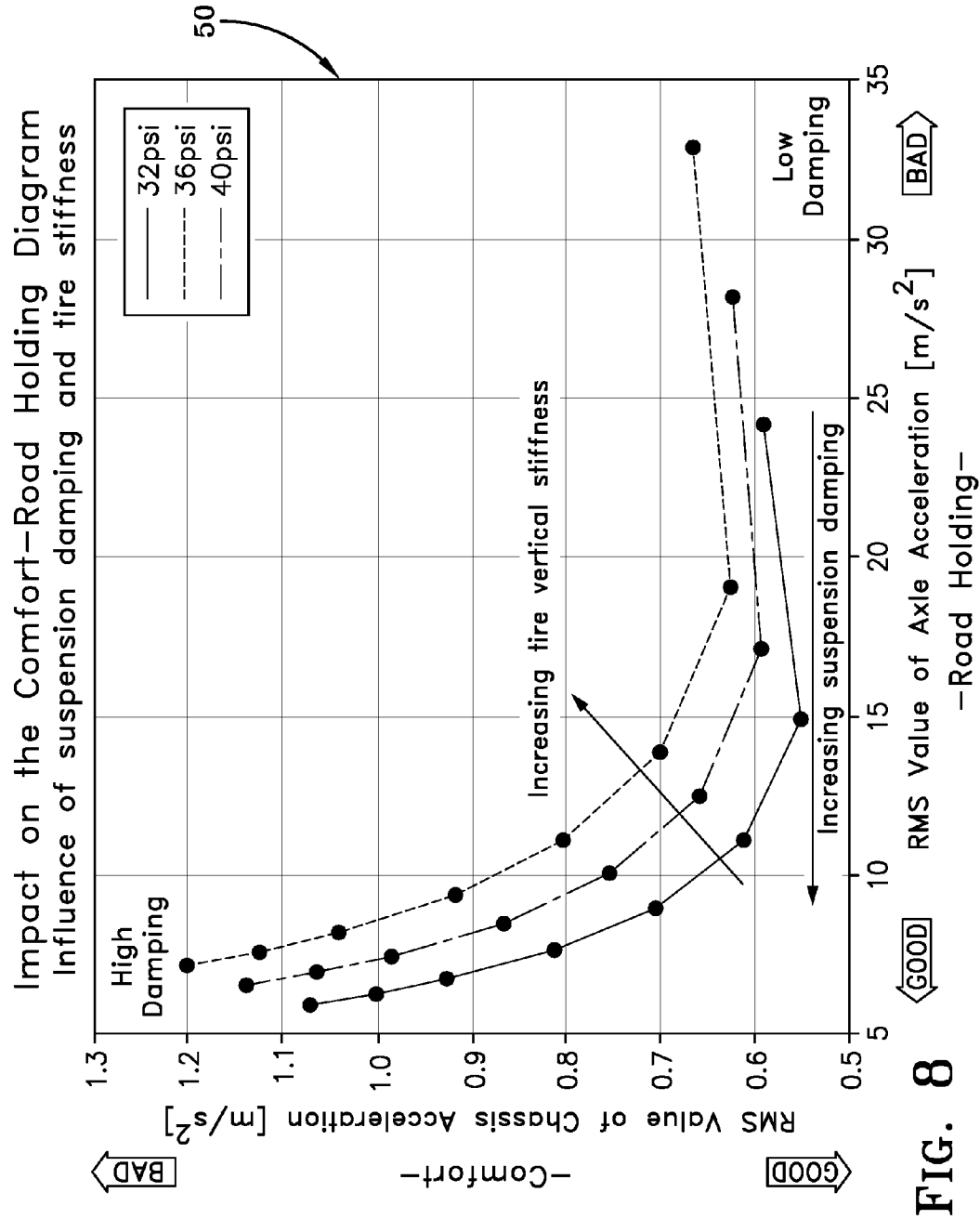
FIG. 8 is a graph showing the impact on the comfort-road holding diagram and the influence of suspension damping and tire stiffness at the three tire inflation levels.

The impact on the comfort-road holding diagram from suspension damping and tire stiffness is seen in graph 50 of FIG. 8. Comfort varies along the vertical axis and road holding along the horizontal axis. RMS value of chassis acceleration to RMS value of axle acceleration is graphed for three tire inflation pressures. Increasing tire vertical stiffness (identified in FIG. 8 by a directional arrow) causes a bad effect on both comfort and road holding while an increase in suspension damping causes a good effect on both comfort and road holding in the curves for all three inflation pressures.

Figure 9B:
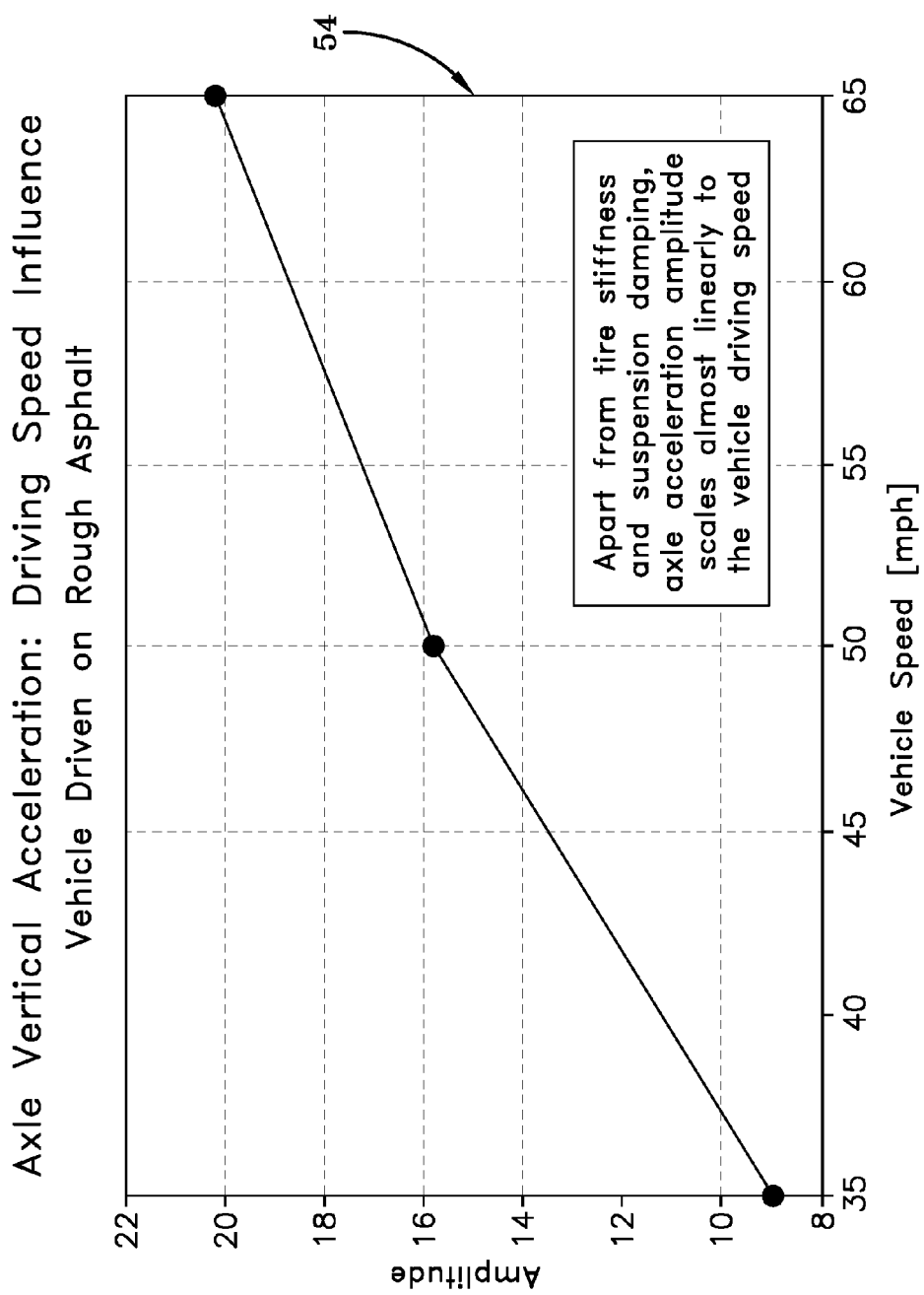
Figure 10A:
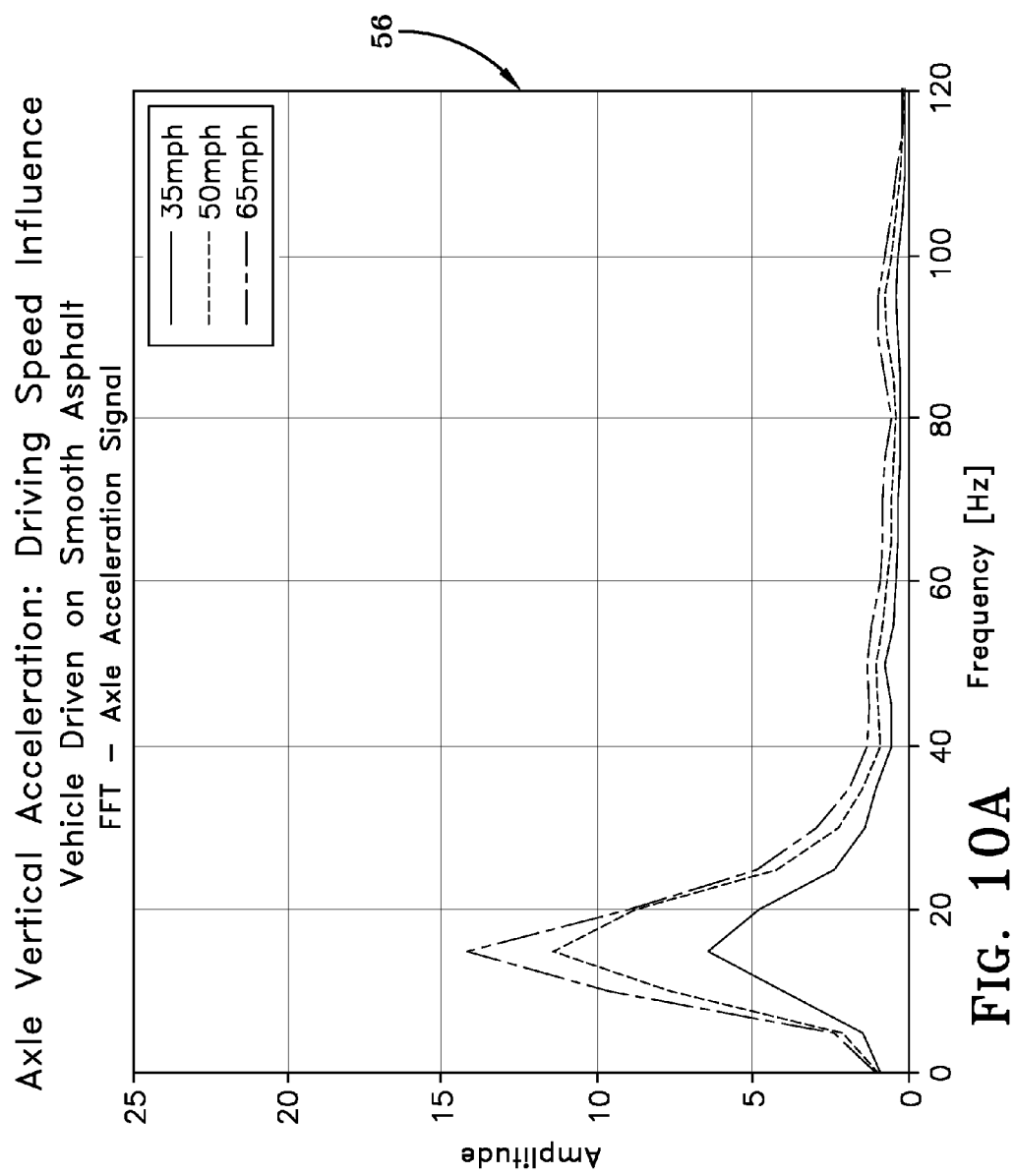
FIGS. 10A and 10B are graphs of axle vertical acceleration of a vehicle driven over smooth asphalt at the three tire inflation levels.
Figure 10B:
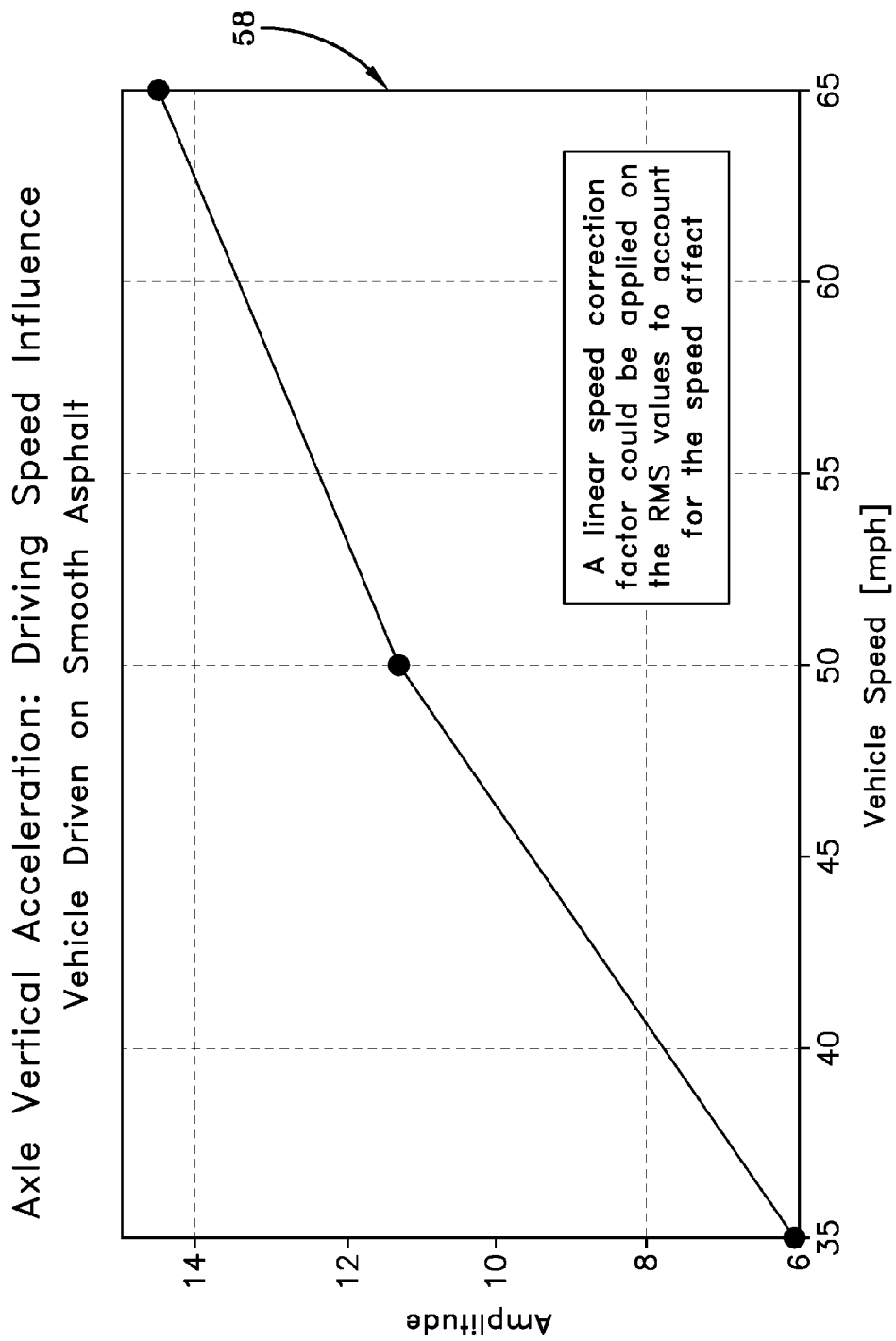

In FIG. 9A, graph 52 shows, for a vehicle driven on rough asphalt, the influence on driving speed on axle vertical acceleration in FFT-axle acceleration signal graphed. Three speeds, 35, 50, and 65 are graphed in graph 52. The graph 52 is used to generate graph 54 in FIG. 9B of amplitude to vehicle speed. The conclusion evidenced is that, apart from tire stiffness and suspension damping, axle acceleration amplitude scales almost linearly to the vehicle driving speed. The test is repeated for smooth asphalt surface and the results are indicated in graphs 56, 58 of FIGS. 10A and 10B, respectively. Again, linearity is indicated for smooth asphalt as with rough asphalt. The subject system thus uses a linear speed correction factor applied to the RMS values to account for this speed affect.

Figure 11:
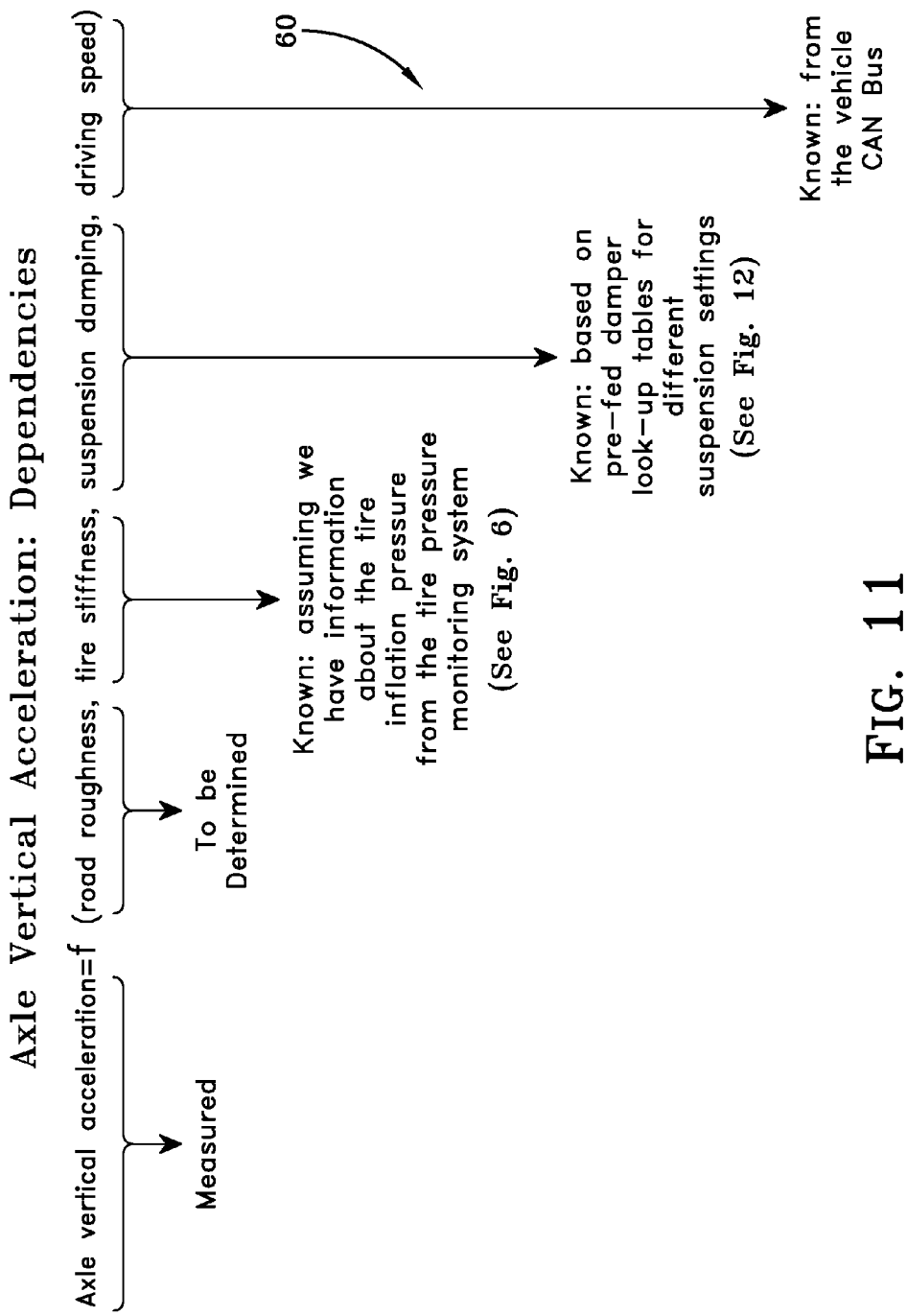
FIG. 11 is a chart showing axle vertical acceleration dependencies.
Figure 12:
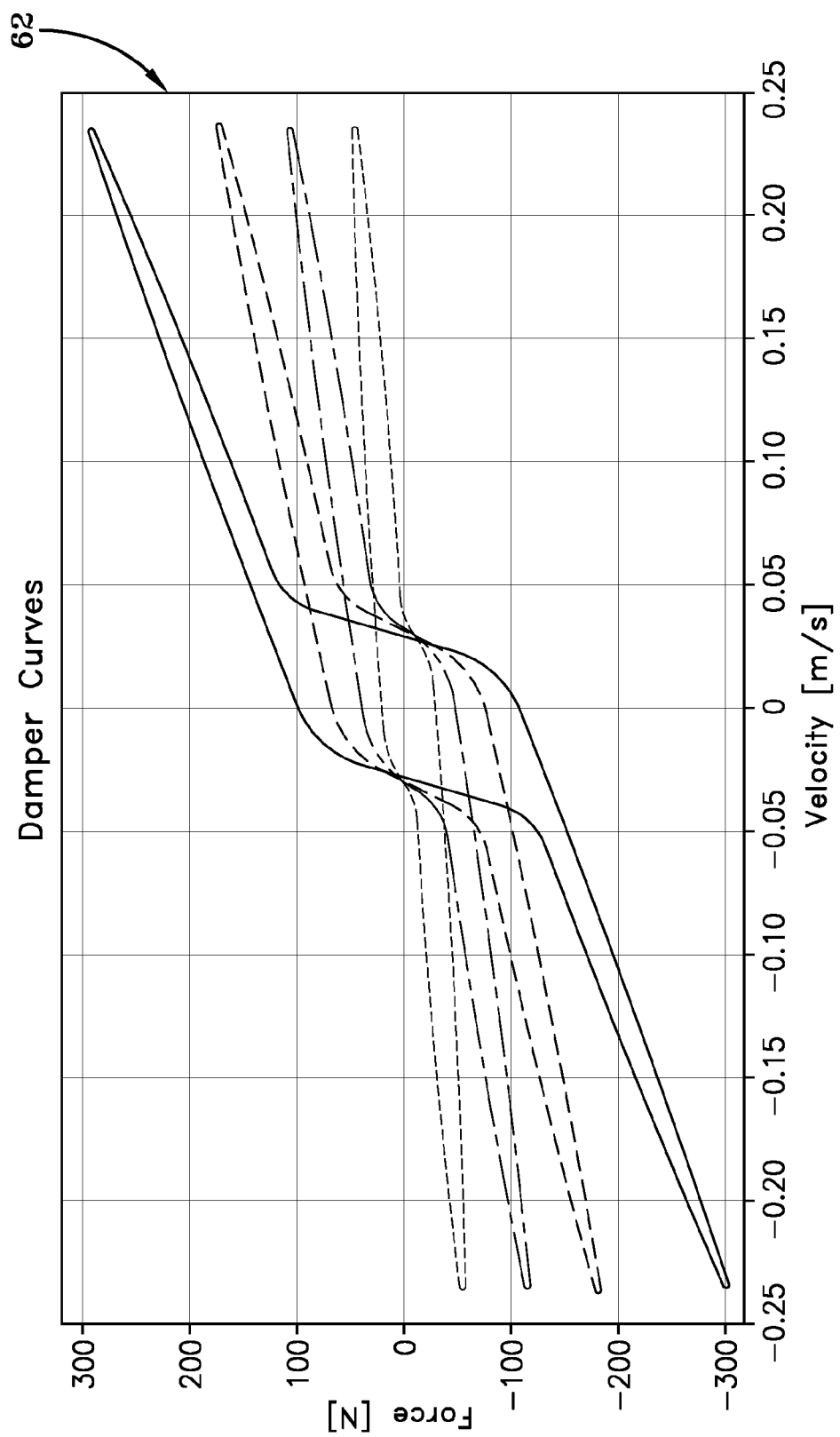
FIG. 12 is a graph showing damper curves.

The dependencies of axle vertical acceleration to road roughness, tire stiffness, suspension damping and driving speed are charted at 60 of FIG. 11. The source of these dependencies is also indicated in FIG. 11. Axle vertical acceleration is a measurement taken from vehicle based and mounted sensors. Road roughness is derived from employment of the subject system and method described herein. Tire stiffness is known from the tire inflation pressure provided from TPMS module 34 for the specific tire identified by the tire ID tag. Suspension damping is known based on pre-fed damper look-up tables for different suspension settings. For example, damper curves 62 shown in FIG. 12 may be used to determine suspension damping. Lastly, driving speed may be obtained from the vehicle CAN-bus. By accounting for and applying the above dependencies, the road roughness may be classified and determined. That is, road roughness classification pursuant to the system and method is determined by combining specific axle vertical acceleration (measured), tire stiffness (using tire ID enabled tire construction and TPMS measured tire inflation), suspension damping (using pre-fed damper look-up tables for different suspension settings) and driving speed (provided by CAN-bus from the vehicle).

Figure 13:
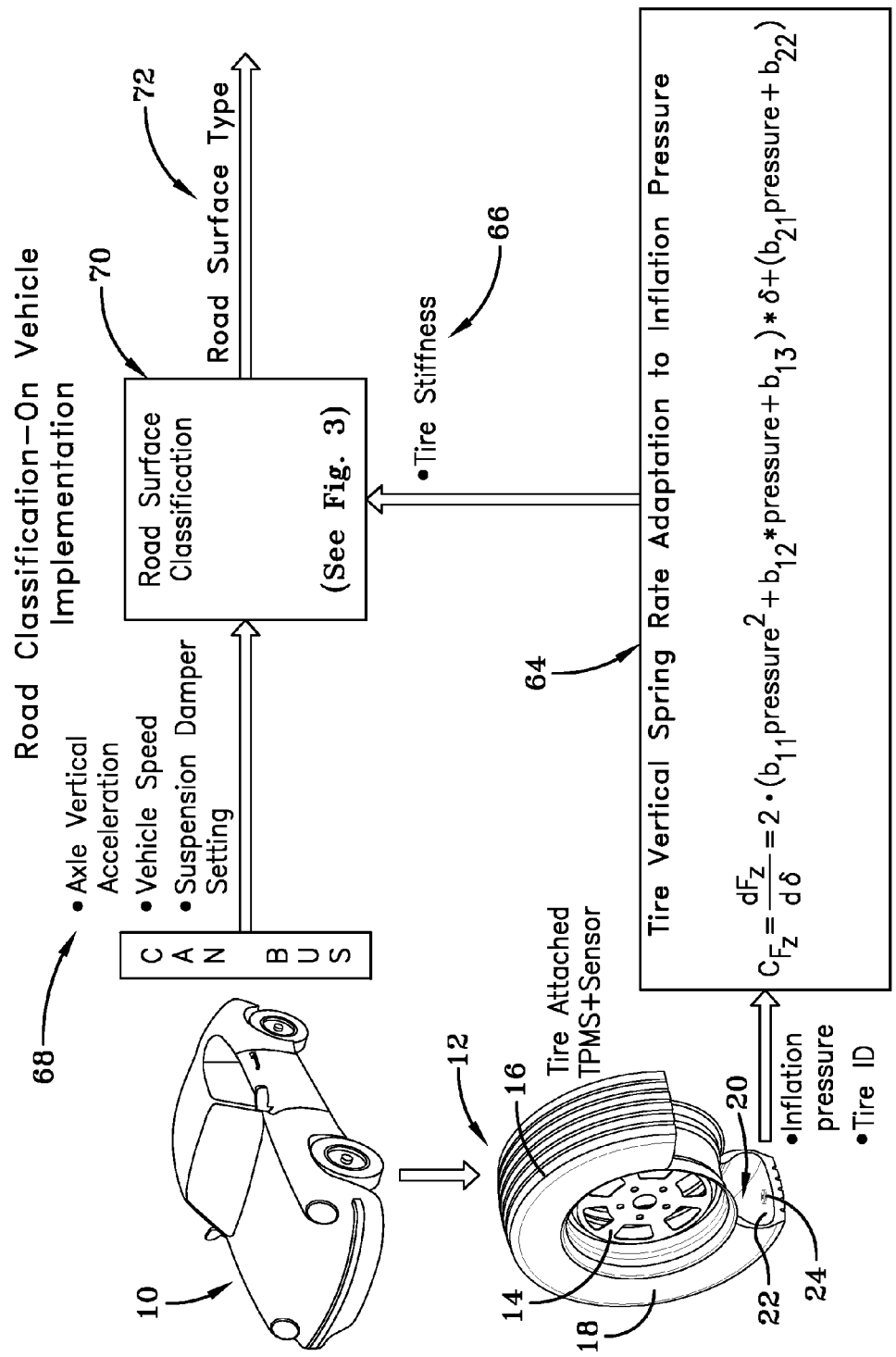
FIG. 13 is a schematic showing road classification—on vehicle implementation.

The above synopsis of the subject system and method are shown schematically in FIG. 13. The vehicle 10 has tires equipped with TPMS modules 24 that will transmit measured tire inflation pressure and tire ID to a processor. Applying the expression 64, using measured tire inflation pressure, the tire vertical spring rate adaptation to inflation pressure is determined. Using the tire vertical spring rate adaptation to inflation pressure and tire identification construction/make enabled by application of the tire ID, a tire stiffness 66 may be determined. Tire stiffness is applied with inputs 68 from the vehicle CAN-bus including axle vertical acceleration, vehicle speed and suspension damper setting to the road surface classification 70. FIGS. 3A and 3B show the vehicle response on smooth and rough surfaces and the RMS chassis acceleration and RMS axle acceleration values from each. While an analysis of the vehicle response is a good beginning in analyzing the condition of the road surface, more accuracy and more robustness is needed for predictable results. The use of tire stiffness 66 is applied to the vehicle response in order to make a tire-specific adjustment in the vehicle response analysis. The tire stiffness 66 is based on TPMS 24 tire-based sensor measurement of inflation pressure and tire ID information, applied through the tire vertical spring adaptation to inflation pressure, in expression 64.

Additionally, the vehicle response graphs of FIGS. 3A and 3B are adapted to the vehicle speed and suspension damper settings available from the vehicle CAN-bus. Vehicle speed and damping curves further enhance the accuracy in analysis of the vehicle response curves and add robustness to the analytic. As a result, the subject system and method of road classification is capable of accounting for the changes in RMS values of axle accelerations due to a variation in the tire inflation pressure or tire construction type/make as well as vehicle speed and suspension damping setting. A more accurate and robust road classification is achieved.

Figure 14A:
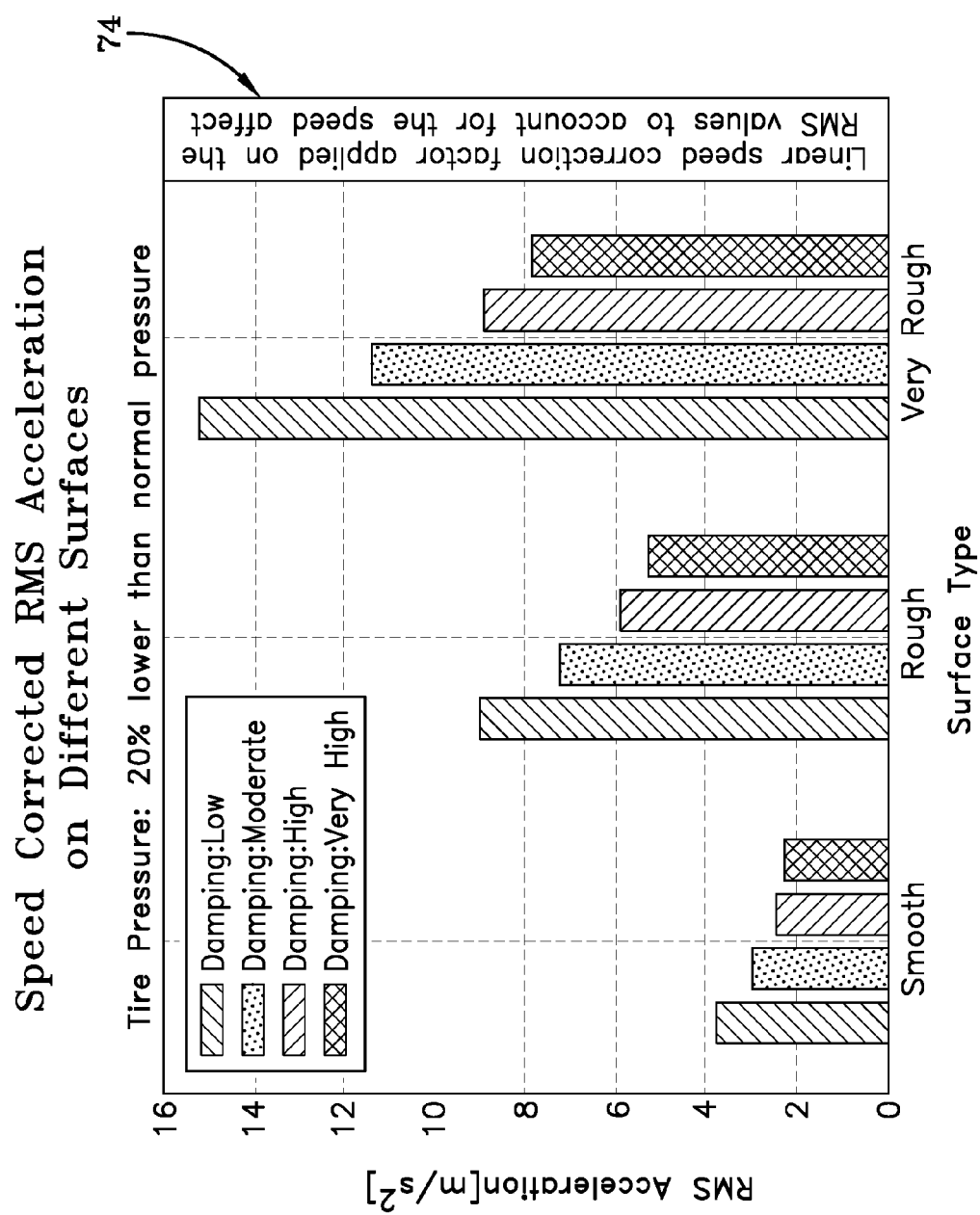
FIG. 14A is a bar chart showing RMS acceleration on different surfaces with tire pressure 20 percent lower than normal.

FIG. 14A shows an empirically derived bar graph 74 on speed corrected RMS acceleration on different road surfaces, showing low, moderate high and very high damping, with the tire inflated 20 percent lower than normal pressure.

Figure 14B:
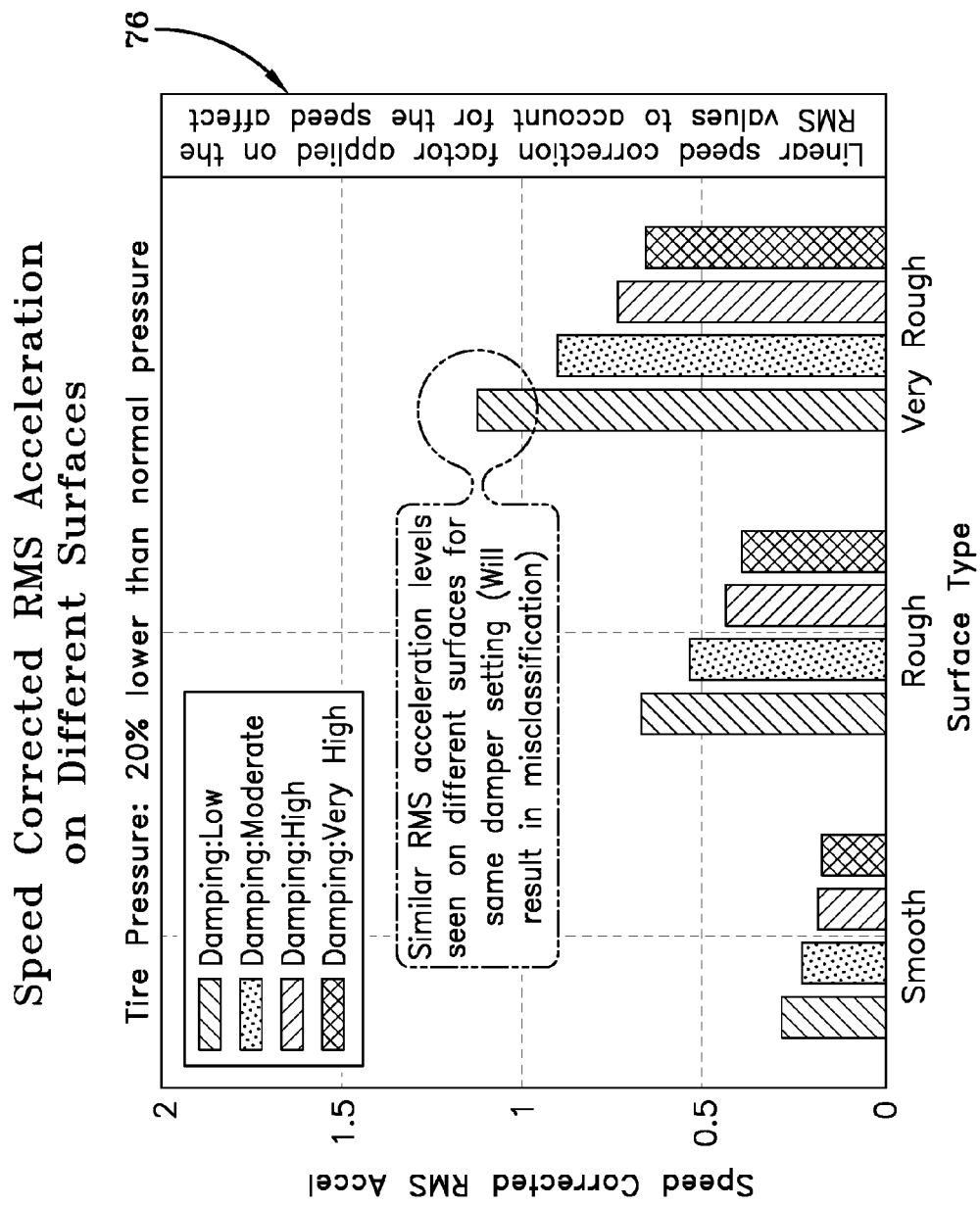
FIG. 14B is a bar chart showing speed corrected RMS acceleration on different surfaces with tire pressure 20 percent lower than normal.

From FIG. 14A, it will be seen that a linear speed correction factor may be applied on the RMS values to account for the speed affect. In FIG. 14B, the bar graph 76 shows speed corrected RMS acceleration on different surfaces at four damping settings for a tire pressure 20 percent below normal. It will be noted that tire inflation is an important factor to the accurate determination of RMS acceleration levels and that similar RMS acceleration levels seen on different surfaces for the same damper setting will result in a misclassification.

Figure 14C:
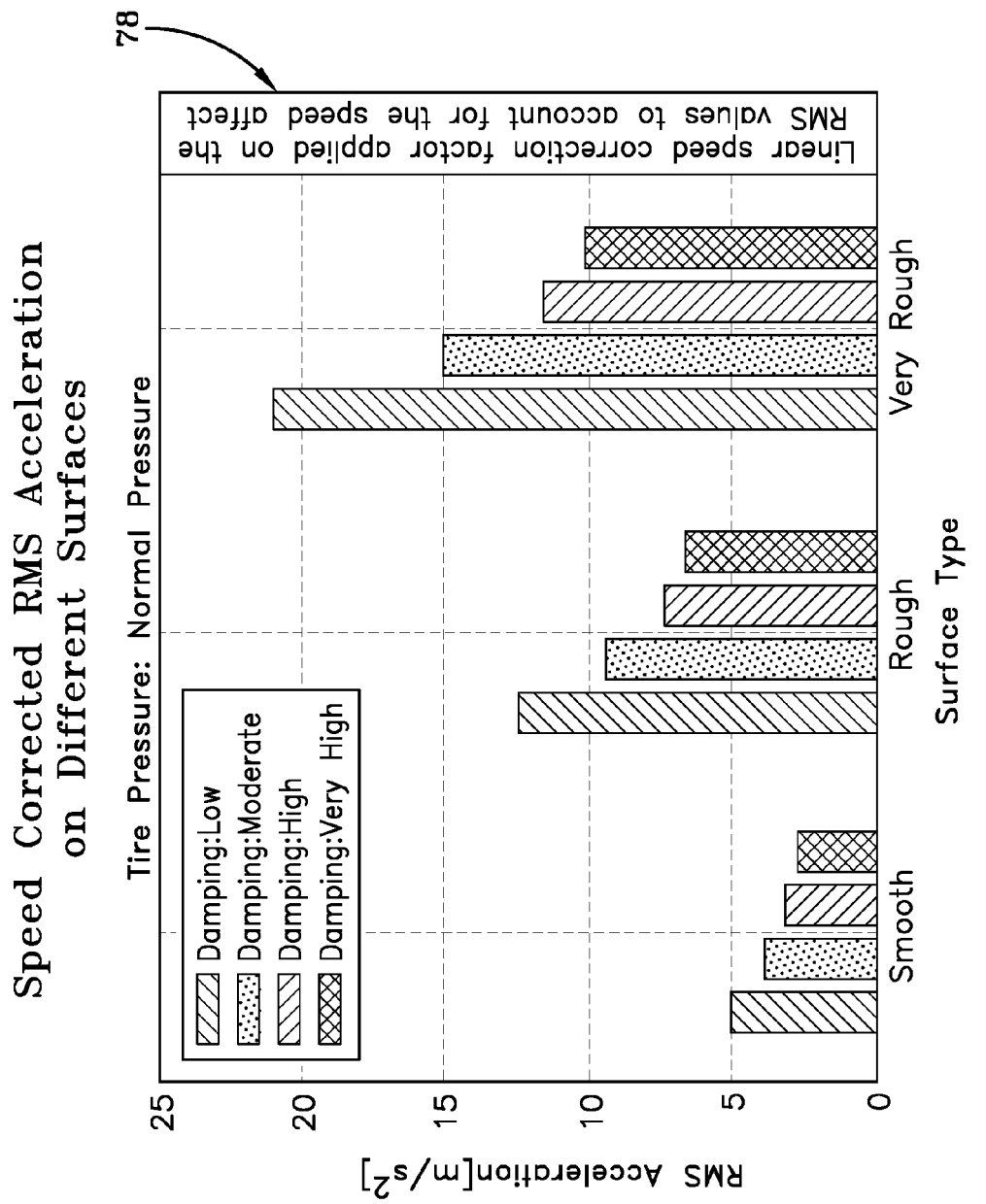
FIG. 14C is a bar chart showing RMS acceleration on different surfaces with tire pressure normal.
Figure 14D:
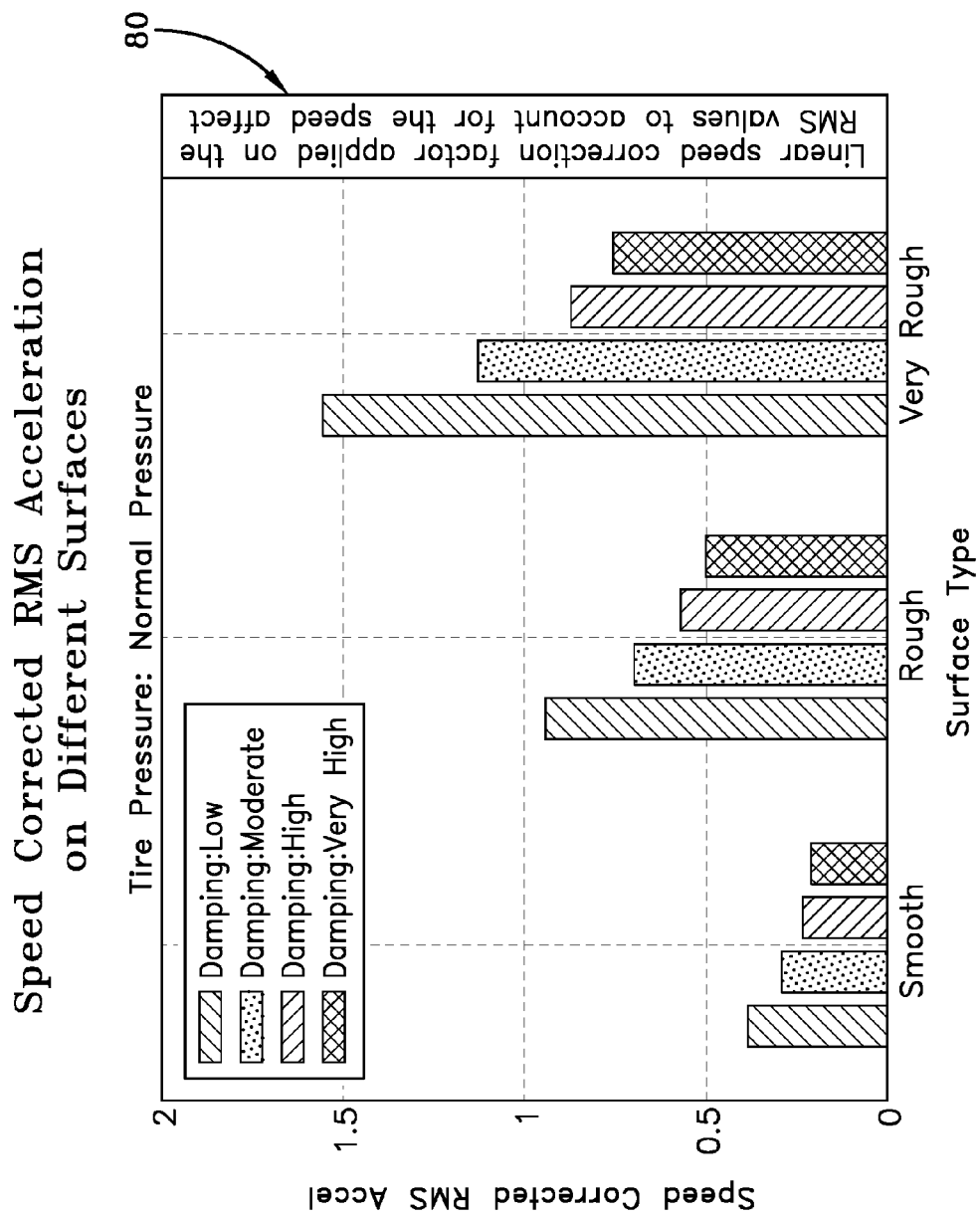
FIG. 14D is a bar chart showing speed corrected RMS acceleration on different surfaces with tire pressure normal.
Figure 14E:
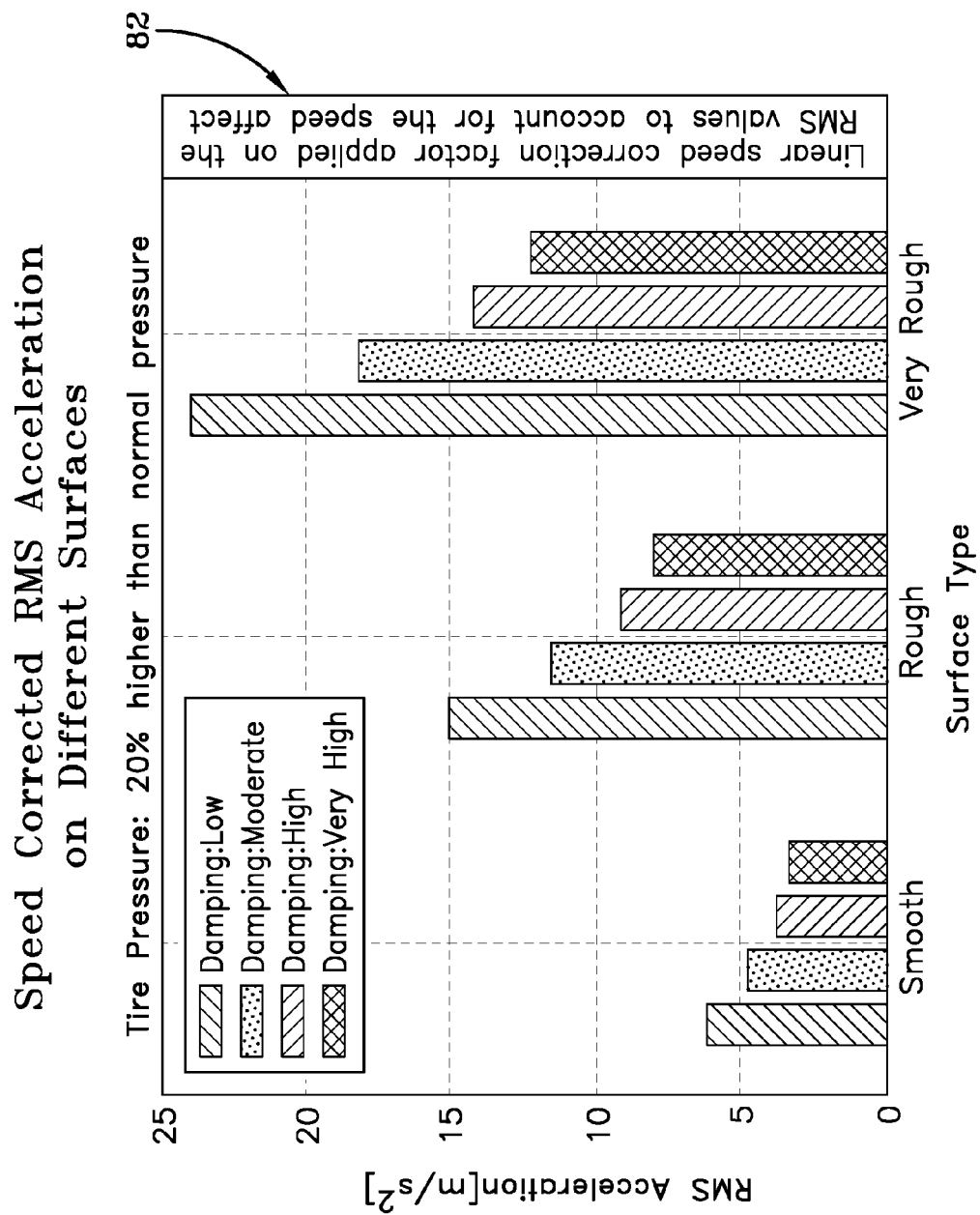
FIG. 14E is a bar chart showing RMS acceleration on different surfaces with tire pressure 20 percent higher than normal.
Figure 14F:
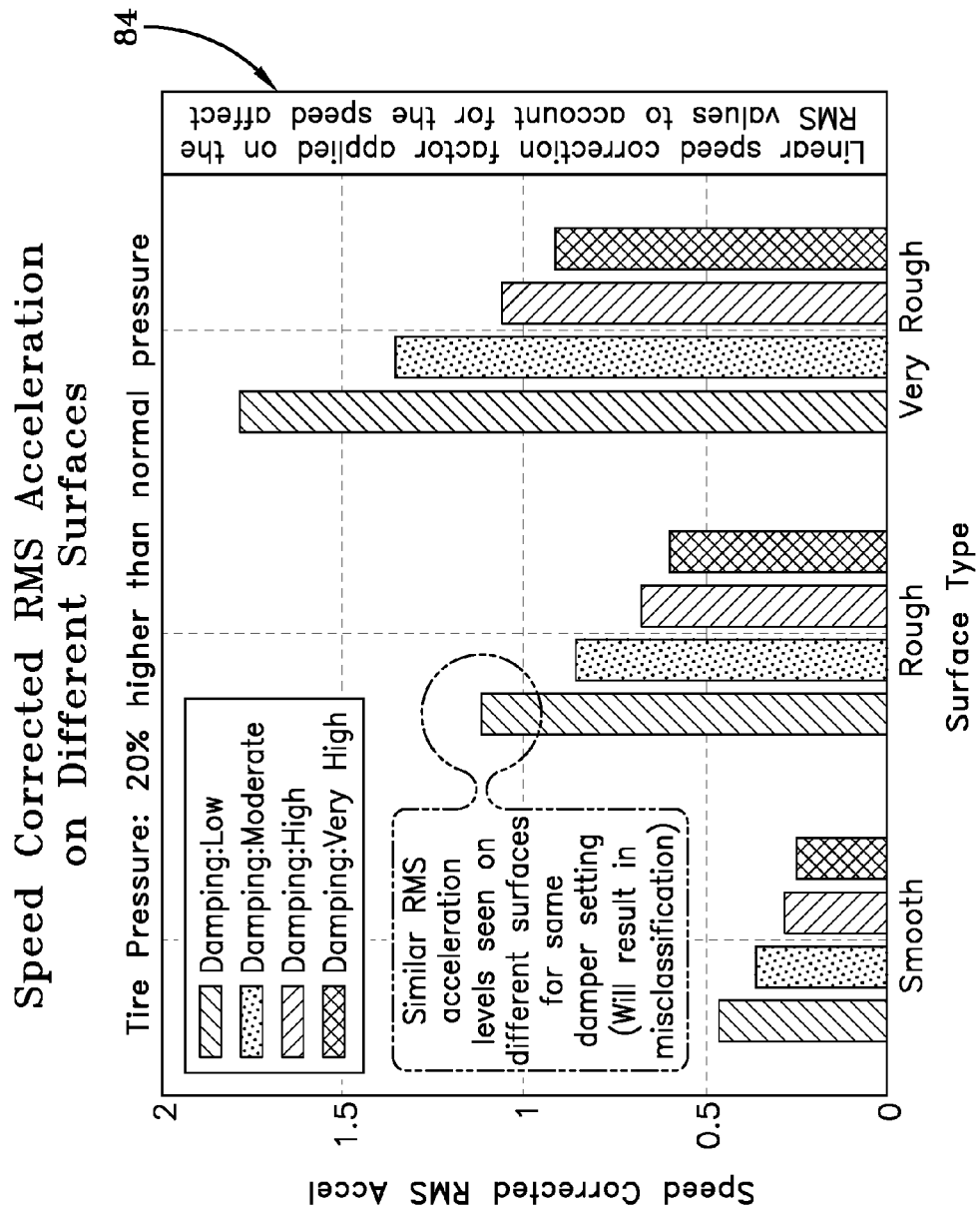
FIG. 14F is a bar chart showing speed corrected RMS acceleration on different surfaces with tire pressure 20 percent higher than normal.

The bar graphs 78, 80 of FIGS. 14C and 14D are for a tire pressure at a normal inflation pressure and may be compared to the graphs 74, 76 (for a 20 percent underinflated tire) to see the effect of inflation level on RMS acceleration levels. Likewise, the bar graphs 82, 84 of FIGS. 14E and 14F for a tire at 20 percent higher inflation pressure may be compared to the underinflated tire graphs 74, 76 and normal tire pressure graphs 78, 80. It will be seen that similar RMS acceleration levels seen on different surfaces for the same damper setting will result in misclassification unless tire inflation pressure is taken into account.

Figure 15A:
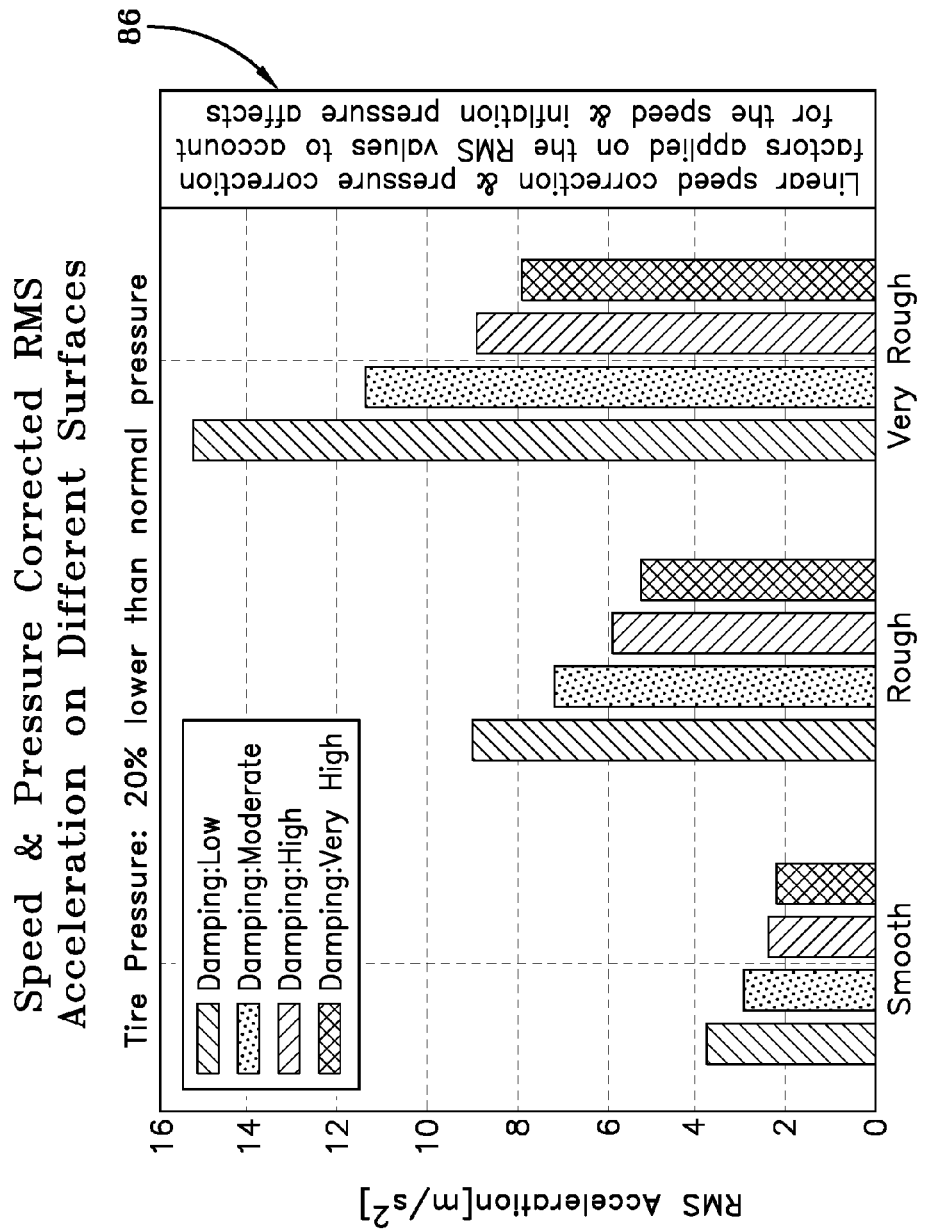
FIG. 15A is a bar chart showing RMS acceleration on different surfaces with tire pressure 20 percent lower than normal.
Figure 15B:
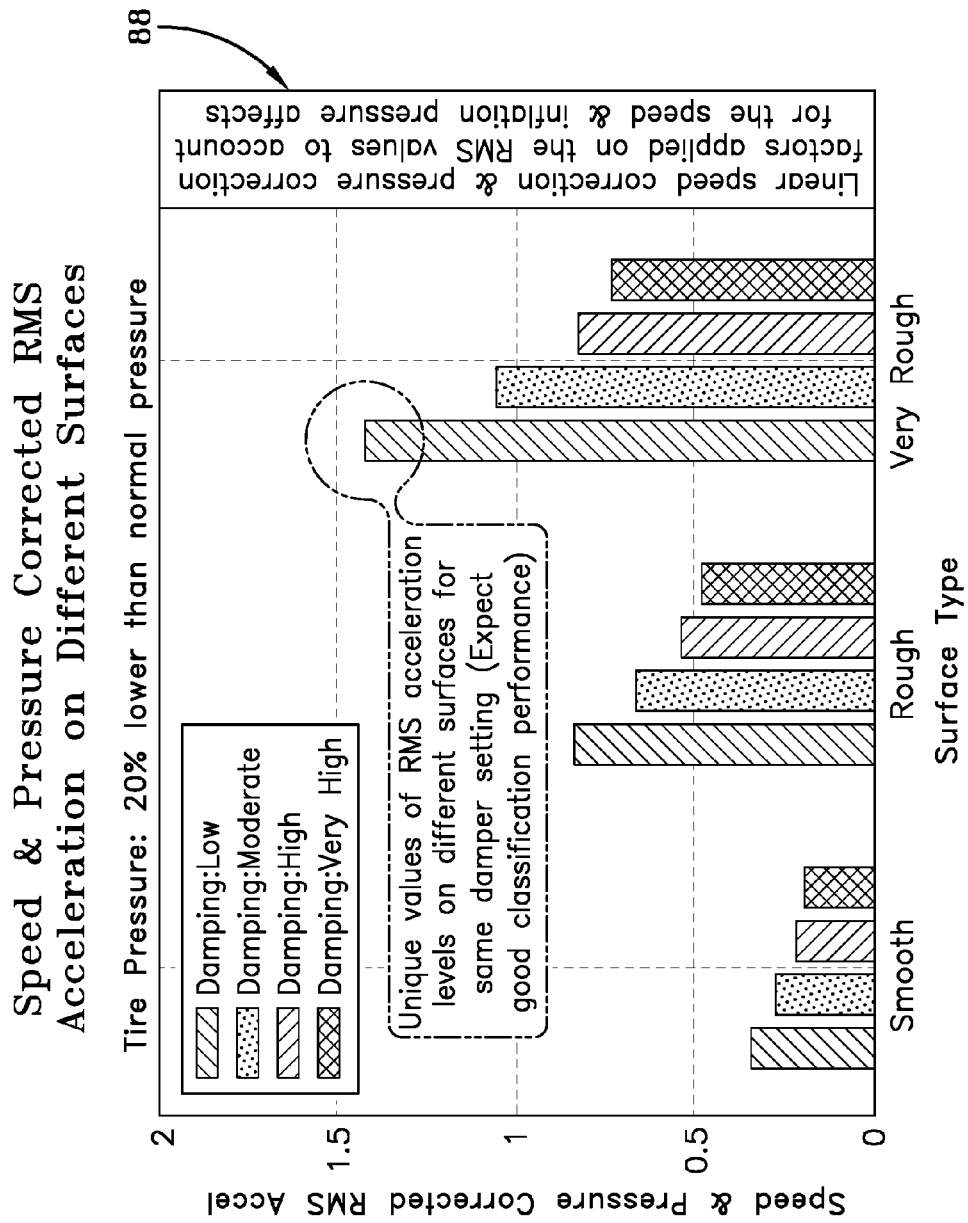
FIG. 15B is a bar chart showing speed and pressure corrected RMS acceleration on different surfaces with tire pressure 20 percent lower than normal.
Figure 15C:
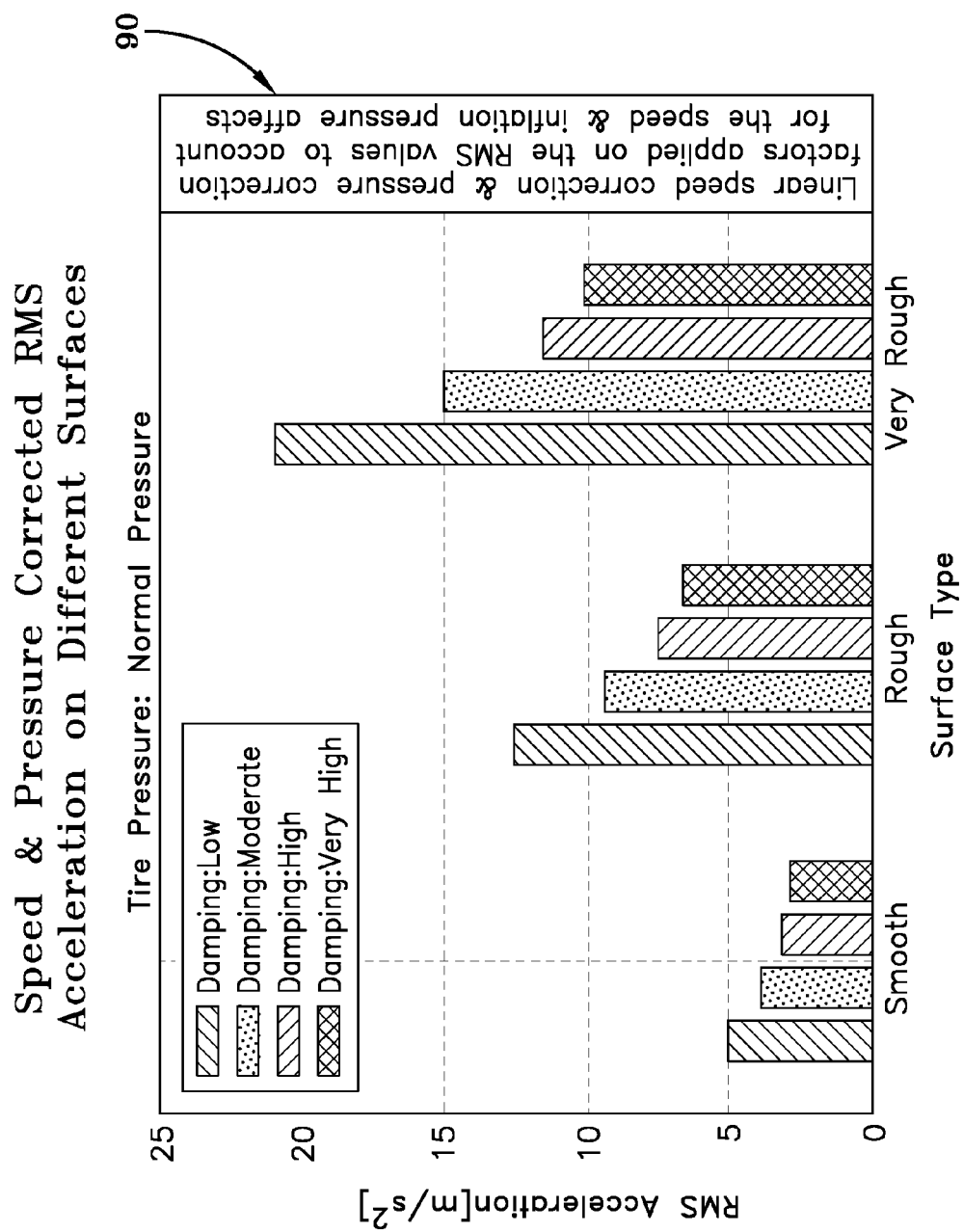
FIG. 15C is a bar chart showing RMS acceleration on different surfaces with tire pressure normal.
Figure 15D:
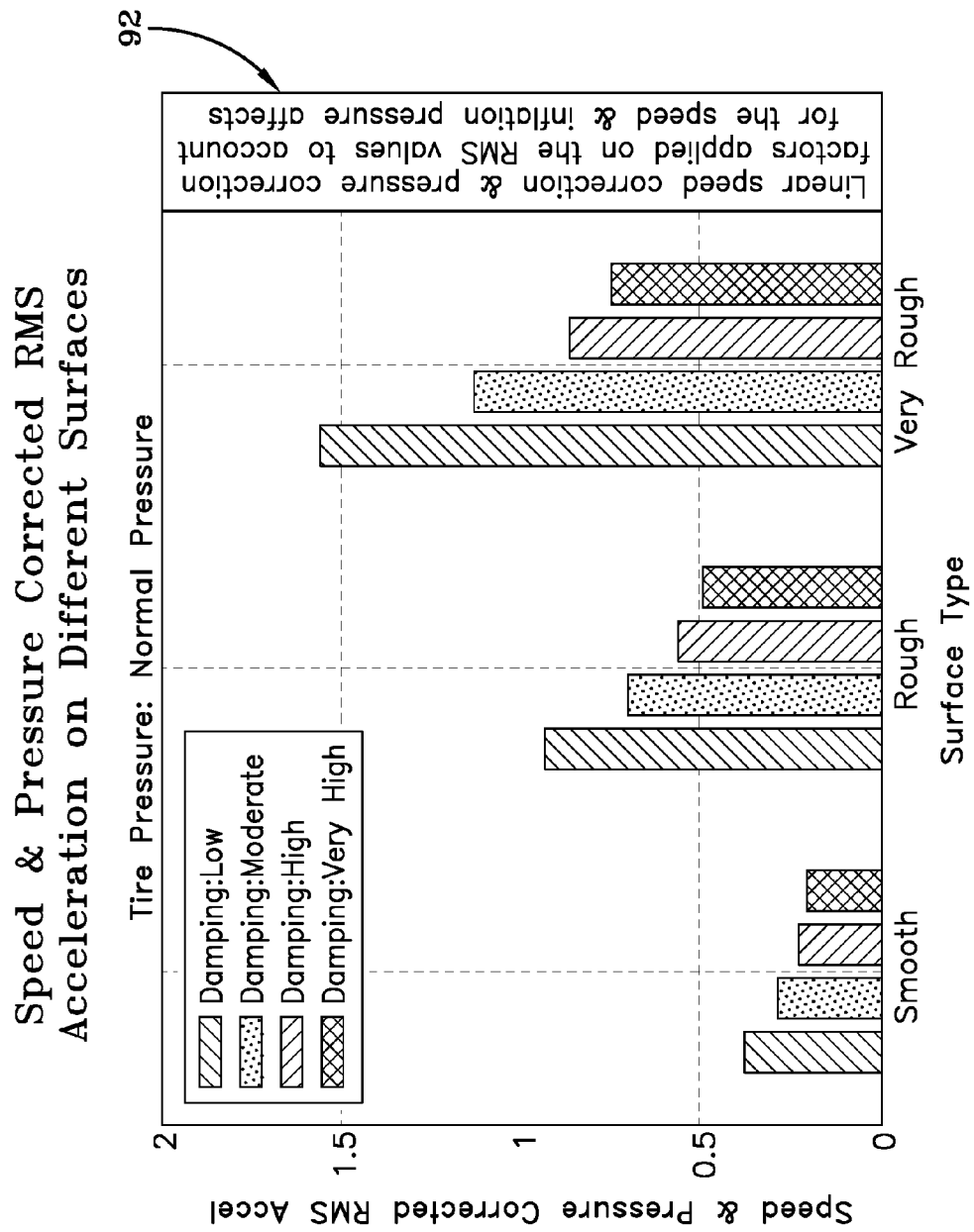
FIG. 15D is a bar chart showing speed and pressure corrected RMS acceleration on different surfaces with tire pressure 20 percent lower than normal.
Figure 15E:
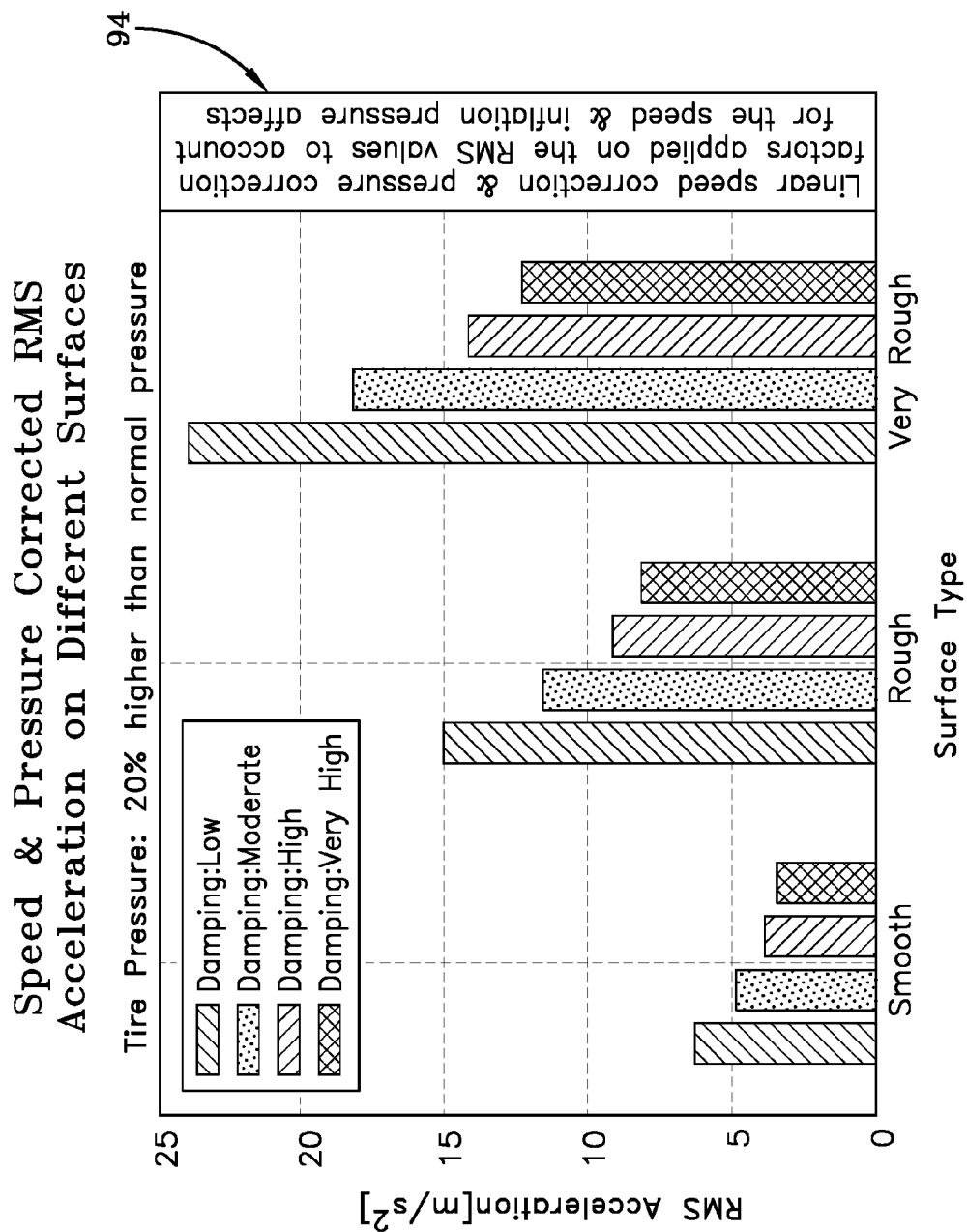
FIG. 15E is a bar chart showing RMS acceleration on different surfaces with tire pressure 20 percent higher than normal.
Figure 15F:
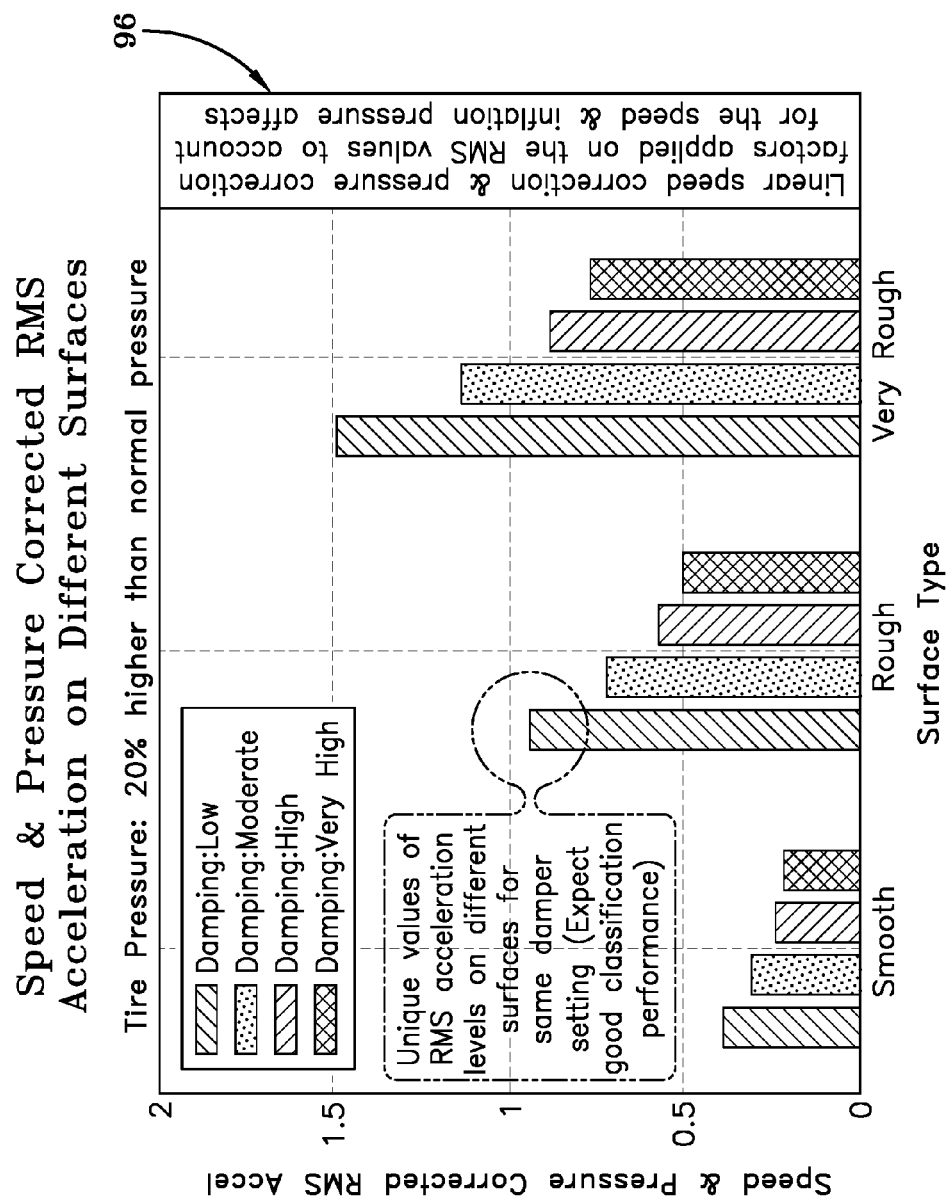
FIG. 15F is a bar chart showing speed and pressure corrected RMS acceleration on different surfaces with tire pressure 20 percent higher than normal.

The bar graphs 86, 88, of FIGS. 15A and 15B show speed and pressure corrected RMS acceleration on different surfaces for a tie 20 percent underinflated. The unique values of RMS acceleration levels on different surfaces for the same damper setting (see identified bar graph amplitude in FIG. 15B) indicate that the system and method achieves superior classification performance by correcting RMS acceleration with speed and pressure. FIGS. 15C and 15D show in bar graphs 90, 92 similar results for a tire at normal pressure. Likewise in FIGS. 15E and 15F show in bar graphs 94, 96 for an overinflated tire, correction for pressure and speed creates unique values of RMS acceleration that can be used to yield a more accurate and robust surface classification.

Availability of a tire attached TPMS module provides tire inflation pressure and tire ID information that enables the implementation of a the subject robust road classification system and method. The classification system and method accounts for the changes in RMS values of axle accelerations due to a variation in the tire inflation pressure or tire type/make.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. A road classification system comprising:
at least one tire supporting a vehicle;
a pressure sensor mounted to the at least one tire and being operable to measure an inflation pressure of the at least one tire;
an identification tag mounted to the at least one tire and being operable to identify the at least one tire by an identification code;
a processor in electronic communication with the pressure sensor to receive the measurement of inflation pressure, and in electronic communication with the identification tag to receive the identification code;
a tire construction database in electronic communication with the processor and being operable for identifying a tire construction type for the at least one tire from the identification code;
a vehicle-mounted axle vertical acceleration sensor operable to measure a vertical acceleration of an axle of the vehicle; and
a road surface classification model in electronic communication with the processor and with the axle vertical acceleration sensor for concluding a road surface condition based on measured changes in an axle vertical acceleration as measured by the axle vertical acceleration sensor and a tire inflation pressure as measured by the pressure sensor and a tire construction type as identified by the identification tag and the tire construction database.

2. The system of claim 1, further comprising a vehicle-mounted speed sensor operable to measure a vehicle speed, wherein the road surface classification model is in electronic communication with the speed sensor and makes the road surface conclusion based on an inclusive consideration of vehicle speed as measured by the speed sensor.

3. The system of claim 1, further comprising a vehicle-mounted sensor operable to indicate a suspension damper setting,
wherein the road surface classification model is in electronic communication with the suspension damper sensor and makes the road surface conclusion based on an inclusive consideration of a suspension damper setting as indicated by the suspension damper sensor.

4. The system of claim 1, wherein the tire inflation pressure as measured by the pressure sensor and the tire construction as identified by the identification tag and the tire construction database are employed in determining a tire sidewall stiffness.

5. The system of claim 1, wherein the road surface classification model makes the road surface condition conclusion based on changes in the axle vertical acceleration as measured by the axle vertical acceleration sensor, a damping of a main suspension of the vehicle as measured by a suspension damper sensor that is in electronic communication with the road surface classification model, and a vertical stiffness of the one tire.

6. The system of claim 5, wherein the vertical stiffness of the at least one tire is calculated based on the tire inflation pressure as measured by the pressure sensor for the tire construction type as identified by the identification tag and the tire construction database.

7. A road classification system comprising:
at least one tire supporting a vehicle;
a pressure sensor mounted to the at least one tire and being operable to measure an inflation pressure of the at least one tire;
an identification tag mounted to the at least one tire and being operable to identify the at least one tire by an identification code;
a processor in electronic communication with the pressure sensor to receive the measurement of inflation pressure, and in electronic communication with the identification tag to receive the identification code;
a tire construction database in electronic communication with the processor and being operable for identifying a tire construction type for the at least one tire from the identification code;

a vehicle-mounted axle vertical acceleration sensor operable to measure a vertical acceleration of an axle of the vehicle;

a vehicle-mounted speed sensor operable to measure a vehicle speed;

a vehicle-mounted sensor operable to indicate a suspension damper setting; and a road surface classification model in electronic communication with the processor and with the axle vertical acceleration sensor, the speed sensor and the suspension damper sensor, for making a road surface condition conclusion based on changes in an axle vertical acceleration as measured by the axle vertical acceleration sensor, the tire inflation pressure as measured by the pressure sensor, a tire construction type as identified by the identification tag and the tire construction database, the vehicle speed as measured by the speed sensor and a suspension damper setting as indicated by the suspension damper sensor.

8. The system of claim 7, wherein the tire inflation pressure as measured by the pressure sensor and the tire construction as identified by the identification tag and the tire construction database are employed in determining a tire sidewall stiffness of the at least one tire.

9. The system of claim 8, wherein the road surface classification model makes the conclusion of road surface condition based on changes in an axle vertical acceleration as measured by the axle vertical acceleration sensor, a damping of a main suspension of the vehicle as indicated by the suspension damper sensor and the determined vertical stiffness of the at least one tire.

10. A method of road classification comprising the steps of:
    mounting an air pressure measuring sensor to a tire supporting a vehicle, the sensor operable to measure a tire inflation pressure of the tire;
    mounting an identification tag to the tire operable to identify the tire by an identification code;
    receiving the measurement of tire inflation pressure and the identification code on a processor that is in electronic communication with the air pressure measuring sensor and the identification tag;
    employing a tire construction database that is in electronic communication with the processor and which is operable to identify a tire construction type for the tire from the identification code;
    mounting an axle vertical acceleration sensor to the vehicle operable to measure an axle a vertical acceleration of an axle of the vehicle;
    employing a road surface classification model in electronic communication with the processor and with the axle vertical acceleration sensor for making a road surface condition conclusion based on changes in an axle vertical acceleration as measured by the axle vertical acceleration sensor, a tire inflation pressure as measured by the air pressure measuring sensor and a tire construction type as identified by the identification tag and the tire construction database.

11. The method of claim 10, further comprising the steps of:
    mounting a speed sensor to the vehicle operable to measure a vehicle speed, wherein the speed sensor is in electronic communication with the road surface classification model; and
    using the vehicle speed as measured by the speed sensor in the road surface classification model to make the road surface condition conclusion.

12. The method of claim 11, further comprising the steps of:
    mounting a sensor to the vehicle operable to indicate a suspension damper setting, wherein the suspension damper sensor is in electronic communication with the road surface classification model; and
    using the suspension damper setting as indicated by the suspension damper sensor to make the road surface condition conclusion.

13. The method of claim 12, wherein the tire inflation pressure as measured by the air pressure measuring sensor and the tire construction as identified by the identification tag and the tire construction database are employed in determining a tire sidewall stiffness.

14. The method of claim 13, further comprising the step of using the determined tire sidewall stiffness in the road surface classification model to make the road surface condition conclusion.

* * * * *